United States Patent [19]
Ebner et al.

[11] Patent Number: 6,005,121
[45] Date of Patent: Dec. 21, 1999

[54] HIGH PRODUCTIVITY PROCESS FOR THE PRODUCTION OF MALEIC ANHYDRIDE

[75] Inventors: Jerry R. Ebner, St. Peters; Robert A. Keppel, Chesterfield; Michael J. Mummey, Lincoln County, all of Mo.

[73] Assignee: Huntsman Petrochemical Corporation, Austin, Tex.

[21] Appl. No.: 09/058,029

[22] Filed: Apr. 10, 1998

Related U.S. Application Data

[62] Division of application No. 07/727,018, Jul. 8, 1991, abandoned.

[51] Int. Cl.$^6$ .................................................. C07D 307/60
[52] U.S. Cl. ............................................ 549/259; 549/260
[58] Field of Search .............................................. 549/259

[56] References Cited

U.S. PATENT DOCUMENTS

| | | | |
|---|---|---|---|
| 3,296,282 | 1/1967 | Kerr | 260/346.8 |
| 3,474,041 | 10/1969 | Kerr | 252/411 |
| 4,342,699 | 8/1982 | Palmer et al. | 549/259 |
| 4,397,772 | 8/1983 | Noakes et al. | 423/213.2 |
| 4,501,907 | 2/1985 | Kwentus et al. | 549/259 |
| 4,515,899 | 5/1985 | Click et al. | 502/35 |
| 4,632,915 | 12/1986 | Keppel et al. | 502/209 |
| 4,701,433 | 10/1987 | Edwards | 502/209 |
| 4,780,548 | 10/1988 | Edwards et al. | 549/259 |
| 4,810,803 | 3/1989 | Edwards | 549/260 |
| 4,855,459 | 8/1989 | Mummey | 549/260 |

FOREIGN PATENT DOCUMENTS

| | | |
|---|---|---|
| 0115879 | 9/1986 | European Pat. Off. . |
| 0099431 | 10/1987 | European Pat. Off. . |
| 1030507 | 5/1966 | United Kingdom .................... 549/257 |

OTHER PUBLICATIONS

Buchanan et al. *Chemical Engineering Communications*, vol. 52, pp. 33–51 (1987).
Calderbank et al. "The Diluted–Catalyst Fixed–Bed Reactor for Exothermic Catalytic Reactions" University of Edinburgh, (cite unknown), pp. 93–106.
Choi et al. "Optimal Catalyst Distribution in a Dual Enzyme Sequential System" *AIChE Journal*, vol. 23, No. 3, pp. 319–326 (1977).
Froment "Fixed Bed Catalytic Reactors—Current Design Status" *Industrial and Engineering Chemistry*, pp. 18–27 (Feb. 1967).
Jenkins et al. "Optimum Catalyst Formulation for the Aromatization of Methylcyclopentane" *The Canadian Journal of Chemical Engineering*, vol. 48, pp. 179–186 (1970).
Orkić et al. "Kinetic Analysis of 1–Butene Oxidation to Maleic Anhydride with a Polyfunctional Catalyst" *Ind. Eng. Chem. Prod. Res. Dev.*, vol. 18, No. 4, pp. 333–339 (1979).
Smith et al. *The Canadian Journal of Chemical Engineering*, vol. 53, pp. 347–349 (1975).

*Primary Examiner*—Bernard Dentz
*Attorney, Agent, or Firm*—Senniger, Powers, Leavitt & Roedel

[57] ABSTRACT

An improved process for the manufacture of maleic anhydride by catalytic oxidation of a nonaromatic hydrocarbon having at least four carbon atoms in a straight chain, in which a gas containing oxygen and hydrocarbon is passed through a fixed catalyst bed in a tubular reactor. The activity of the catalyst bed is graded in such manner that the reactor can be operated at an initial (feed gas) hydrocarbon concentration of over 1.5% by volume, an integrated average temperature difference between gas and cooling fluid of at least about 15° C. over that portion of the bed in which the gas temperature exceeds the cooling fluid temperature, and a productivity of at least about 5.0 lbs. maleic anhydride per hour, without the temperature difference between the gas and the cooling fluid exceeding 80° C. at any point in the catalyst bed during the course of the reaction. Preferably, the catalyst activity and the gas permeability of the bed vary in the direction of gas flow so that both the catalyst activity and the pressure drop per unit distance are lower in a critical region, where the combination of temperature and hydrocarbon concentration could otherwise cause the reaction to proceed at an excessive rate, than they are in a region of low temperature and low hydrocarbon concentration. Significant and unexpected improvement in reactor performance is achieved by the combination of a graded catalyst charge and incorporation of a catalyst modifying organophosphorus compound in the hydrocarbon feed.

44 Claims, 1 Drawing Sheet

HIGH PRODUCTIVITY PROCESS FOR THE PRODUCTION OF MALEIC ANHYDRIDE

This application is a divisional of Ser. No. 07/727,018, filed on Jul. 8, 1991 now abandoned.

BACKGROUND OF THE INVENTION

This invention relates to the field of catalytic oxidation of hydrocarbons to produce oxygenated hydrocarbons, and more particularly to an improved process for the preparation of maleic anhydride and other oxygenated hydrocarbons at enhanced productivity.

Conventionally, maleic anhydride is manufactured by passing a gas comprising n-butane and oxygen through a fixed catalyst bed tubular plug flow reactor containing a catalyst that consists of mixed oxides of vanadium and phosphorus. The catalyst may contain minor amounts of promoters or activators such as iron, lithium, zinc, chromium, uranium, tungsten, various other metals, boron and/or silicon. Other nonaromatic hydrocarbon starting materials which contain at least four carbon atoms in a straight chain, for example, 1-butene, 2-butene, 1,3-butadiene and mixtures thereof, can also be used in the process. The hydrocarbon starting material reacts with the oxygen to produce maleic anhydride and various by-products, including carbon monoxide and carbon dioxide.

The oxidation of n-butane or other of the above-mentioned starting materials is highly exothermic. Conversion of n-butane to maleic anhydride releases about 350 kCal/mole. Conversion to carbon dioxide, which is equivalent to combustion of the n-butane, releases about 650 kCal/mole. Thus, a substantial amount of heat must be removed in the course of the reaction. Conventionally, a shell and tube heat exchanger is used as a reactor, with the catalyst packed in the tubes, through which the reactant gases are passed. A cooling fluid, typically molten salt, flows over the outsides of tubes. Because the length to diameter ratio of the tubes is high, the reaction system approaches plug flow. The cooling capacity is substantially uniform throughout the reactor, but the rate of reaction varies widely with the concentration of hydrocarbon reactant and temperature. Because the reactant gases are normally introduced into the catalyst bed at a relatively low temperature, the reaction rate is low in the region near the inlet, despite the fact that hydrocarbon concentration is at its maximum at this point. As the gas temperature increases due to initial reaction, heat is generated at a rate that increases as a function of distance in the direction of gas flow, requiring the gas temperature to rise as a function of distance in order that the cooling rate per unit of tube length balances the rate of heat generation per unit of tube length. The temperature continues to increase with distance along the length of the reactor tube until a point is reached at which depletion of the hydrocarbon causes the rate of heat generation to slow, allowing the remainder of the reactor to operate at a lower temperature differential. Thus a point of maximum temperature is reached, which is generally referred to as the "hot spot" of the reactor. When the reactor is under proper control, the hot spot occurs in an intermediate region of the catalyst bed, and from this point downstream to the gas exit, the temperature typically declines.

Problems occur in operation of the reactor if the hot spot temperature becomes too high; and especially serious problems can arise if it propagates or migrates to the exit of the reaction zone. Typically, the salt bath cooling fluid is maintained at a temperature of about 380° to about 460° C. If the gas temperature exceeds about 500° C., or the difference between the gas temperature and the salt bath temperature is greater than about 80° C., the catalyst degrades at an accelerated rate due to sintering or other effects, resulting in a progressive decline in the productivity of the plant and, in some instances, the selectivity of the catalyst. Moreover, because the reaction rate constant increases exponentially with temperature, the reaction can run away if the gas temperature substantially exceeds a temperature 80° C. higher than the cooling fluid. Additionally, higher temperatures tend to favor the complete oxidation of the hydrocarbon to $CO_2$ and water. This not only reduces the yield and productivity of desired product, but the higher heat of reaction released in conversion to $CO_2$ compounds the problem by further increasing the temperature.

Excessive deactivation of catalyst due to thermal degradation can cause the hot spot to migrate to the exit end of the catalyst bed. In this case, it becomes necessary to lower the hydrocarbon concentration or space velocity. Otherwise, the exit gas may contain sufficient unreacted hydrocarbon to create risk of an uncontrolled reaction in downstream equipment. Reducing the hydrocarbon or space velocity results directly in a loss of productivity.

Accordingly, it has been a high priority in the art to design and operate maleic anhydride and other catalytic oxidation reactor systems to control both the magnitude and location of the temperature peak, the so-called hot spot of the reaction. Efforts have also been directed to developing systems in which the reactor temperature profile is as even as possible, thereby allowing operation at higher average temperature for higher productivity.

Catalyst packs having graded activity in the direction of gas flow have been proposed to meet various objectives. Such catalyst systems generally include a region of relatively low activity where the so-called hot spot of the reactor occurs in order to minimize the temperature peak at that hot spot. This stratagem serves several purposes. First, it helps to protect the system against the runaway reactions that can occur if the hot spot temperature peaks too high. If the catalyst activity is relatively low in such region, the resultant reaction rate moderation prevents the temperature from rising as high as it otherwise generally would. Moreover, at a given temperature, the reaction rate is relatively low, so that self-acceleration into dangerous conditions is inhibited. Controlling the temperature peak favors the preferred reactions in competition with the high activation energy side reactions that produce CO and $CO_2$. It also minimizes the rate of degradation of the catalyst, which increases with temperature. Additionally, it allows operation at higher than conventional temperatures upstream and especially downstream of the hot spot, without risking runaway reaction, thereby providing a higher overall rate of heat dissipation, equating to a higher rate of production.

Palmer et al. U.S. Pat. No. 4,342,699 describes a process for the manufacture of maleic anhydride using a fixed catalyst bed that is graded so that reactivity increases over a least a portion of the effective reaction zone length from minimum activity nearest the feed end of the reaction zone to maximum activity nearest the exit end. Maleic anhydride is removed from the reactor effluent and unreacted n-butane is recycled to the feed end after a purge for removal of inerts. The composition of the feed gas is on the hydrocarbon rich side of the flammability envelope. The combination of n-butane rich feed and graded catalyst is said to result in improved productivity of maleic anhydride as compared to processes that do not use this combination of features.

Palmer et al. prefer that the entire effective length of the reaction zone is graded from minimum activity at the feed end to maximum activity nearest the exit end, but also contemplate grading only a portion of the effective length in such manner, providing a zone of high or intermediate activity at the inlet end to provide a preheating zone. Palmer et al. describe grading of catalyst activity by dilution with inert particles having a size and shape at least roughly similar to the catalyst pellets. Several other methods for achieving the desired activity gradient are mentioned. One is to employ a supported catalyst in which the proportion of support decreases, and correspondingly the proportion of active catalyst increases, from the minimum to the maximum reactivity zones. Another is to partially impregnate a support with catalyst. A third is to use different catalysts, or varying blends of different catalysts, in the individual reactivity zones.

Mummey U.S. Pat. No. 4,855,459 describes an improved process for the catalytic oxidation of various $C_4$ hydrocarbons to maleic anhydride under conditions sufficient to provide a single pass conversion of at least 70% of the hydrocarbon fed. The catalyst is diluted with inert solid material effective to stabilize the maleic anhydride yield such that the average yield decay is less than 0.30% of the established maleic anhydride yield per month over an extended period of sustained operations. Alternatively, a supported catalyst is used and the proportion of active catalyst on the support increases from the maximum to the minimum dilution stage. In the process of the '459 patent, suitable configurations for the diluted catalyst pack are not narrowly critical and vary depending upon overall catalyst pack length, production rate, composition of the active catalyst, reaction conditions and the like. Nonlimiting examples include (a) a configuration in which the diluted catalyst pack is graded in dilution such that dilution decreases over at least a portion of the catalyst pack length from maximum dilution nearest the feed inlet end to minimum dilution nearest the exit end and (b) a configuration in which a first portion of the catalyst pack, proceeding from the feed inlet end to the exit end, has minimum dilution and the remainder of the catalyst pack is graded from maximum dilution nearest the feed inlet end to minimum dilution nearest the exit end. In the latter case the initial minimum dilution zone is relatively short and can serve as a preheating zone for the gas feed stream. The catalyst pack is graded in dilution such that the minimum dilution occurs within that region of the reaction zone which extends over the initial 50% of the length of the catalyst pack in which the hottest point of the reaction zone is located.

Smith and Carberry, "On the Use of Partially Impregnated Catalysts for Yield Enhancement in Non-Isothermal Non-Adiabatic Fixed Bed Reactors," *The Canadian Journal of Chemical Engineering*, 53, pp. 347–349 (1975) discloses the use of catalyst pellets that are partially impregnated with active catalyst in the oxidation of naphthalene to phthalic anhydride. The paper reports the results of varying both the fraction of pellet radius occupied by deposited catalyst and the total amount of catalyst deposited. Partial impregnation was found to improve yields. By comparison with partially impregnated catalyst, tests with fully impregnated catalyst required relatively small catalyst particles, higher pressure drop and consequently higher inlet gas pressure. This reference mentions the use of different catalyst in zones of the bed in which different steps of a multi-step reaction predominantly occur, but does not disclose the grading of catalyst impregnation or pellet size along the length of the reactor.

Buchanan and Sundaresan, "Optimal Catalyst Distribution and Dilution in Nonisothermal Packed Bed Reactors," *Chem. Eng. Comm.*, 1987, Vo. 52, pp. 33–51 presents conditions for optimal loading with a two-dimensional reactor model and applies them to catalyst dilution in a butane oxidation reactor. The reference refers to catalyst dilution with inerts as an important special case of non-uniform catalyst loading, and notes that under some circumstances a chemically non-uniform catalyst loading may be preferable to simple physical dilution with inerts. In discussing certain other references that describe chemically non-uniform catalyst, Buchanan et al. speculate that the motivation to use them may depend partly on the convenience of the various catalyst preparation procedures or on considerations of catalyst longevity. They note that, for the vanadium catalyst used for $C_4$ oxidation, higher phosphorus content in the vicinity of the hot spot may help stabilize the catalyst against deactivation. They further observe that one opportunity for chemical variation arises when there is an inverse relationship between activity and selectivity. In oxidation of both butane and butene, as the phosphorus content of the catalyst increases, overall activity declines but selectivity to maleic anhydride increases. Buchanan et al. present data showing the effect of various catalyst dilution schemes on yield of desired product.

Kerr U.S. Pat. No. 3,474,041 describes the addition of an organophosphorus compound for reactivation of mixed vanadium and phosphorus oxide catalyst for the oxidation of butane to maleic anhydride. Various means for introducing the organophosphorus compound into the catalyst bed are described including introduction of the phosphorus compound into the butane and oxygen containing feed gas to the reactor. Best results are said to be obtained by adding the organophosphorus compound after discontinuing hydrocarbon flow and blowing the reactivated catalyst with air prior to the re-introduction of hydrocarbon. The reference notes that the phosphorus compound can serve as a stabilizer as well as a reactivator for the catalyst.

Click, et al., U.S. Pat. No. 4,515,899 describes steam regeneration of phosphorus treated vanadium/phosphorus/oxygen catalyst for maleic anhydride. The reference notes that treatment of the catalyst with phosphorus compound reduces activity but increases selectivity, the loss of activity being compensated for by an increase in temperature of the reaction. The reference reports that, in practice, it is found that phosphorus compounds concentrate near the feed end of the reactor, thus requiring that the amount of phosphorus addition be limited. Addition of steam after treatment with phosphorus compound re-distributes the phosphorus compound more evenly through the reaction zone.

Edwards U.S. Pat. No. 4,701,433 applies both water and a phosphorus compound in situ in amounts sufficient to partially deactivate a portion of the catalyst. Edwards teaches that the addition of the combination of phosphorus compound and water serves to deactivate the region in which the hot spot of the reaction occurs, thereby moving the hot spot downstream and apparently allowing for reactivation of the region in which the hot spot previously occurred. A similar disclosure is contained in Edwards U.S. Pat. No. 4,810,803. Both references disclose the use of alkyl phosphates and alkyl phosphites for such purpose.

Edwards U.S. Pat. No. 4,780,548 also describes a process for reactivation of a phosphorus/vanadium/oxide catalyst for the oxidation of n-butane to maleic anhydride.

Although the literature is replete with publications which discuss various aspects and purposes of catalyst activity modification in the fixed bed catalytic oxidation of hydrocarbons, a need has remained for catalyst systems which provide for the manufacture of maleic anhydride with maximum productivity.

Productivity of a catalytic oxidation system for the manufacture of maleic anhydride can be defined by the equation:

$$\text{productivity} = \frac{\text{lbs. maleic anhydride produced}}{\text{ft}^3\text{-catalyst-hr.}}$$

$$= 2.58 \times 10^{-5} \times$$

$$(\% \text{molar yield maleic})(\text{GHSV})(\text{mole}\% \ C_4 \text{ in feed})$$

where GHSV is the gas hourly space velocity ($hr^{-1}$). Computations indicate that the productivity can be converted to metric units by applying the factor 16.0, leading to the relationship:

$$\text{productivity} = \frac{\text{kg maleic anhydride produced}}{\text{m}^3\text{-catalyst-hr.}}$$

$$= 4.14 \times 10^{-4} \times$$

$$(\% \text{molar yield maleic})(\text{GHSV})(\text{mole}\% \ C_4 \text{ in feed})$$

Molar yield in turn is the product of conversion and selectivity. Conversion is a function of a number of operating variables including, but not limited to, temperature, space velocity and active catalyst density in the reactor tube. Because the reaction rate constant is highly temperature dependent, molar yield and productivity necessarily depend on the ability to operate the reactor at a relatively high average temperature without suffering runaway reaction, excess $CO_2$ formation or catalyst degradation due to excess hot spot temperature.

Pressure drop through the reactor system is another variable which materially affects the productivity and performance of the reaction system. To achieve the same space velocity at high pressure drop not only consumes mechanical energy, but requires a higher hydrocarbon partial pressure at the reactor inlet. Because the hot spot temperature and tendency to runaway may be highly sensitive to the partial pressure of the hydrocarbon reactant, high pressure drop may require the initial hydrocarbon content of the gas to be curtailed to reduce the parametric sensitivity of the system, thus adversely affecting the productivity.

SUMMARY OF THE INVENTION

Among the several objects of the present invention, therefore, may be noted the provision of an improved process for producing maleic anhydride in high productivity by catalytic oxidation of n-butane or other hydrocarbon gas; the provision of such a process which produces maleic anhydride in high yield; the provision of such a process which utilizes a catalyst system that prevents runaway reactions with minimum adverse effect on productivity; the provision of such a process which operates at relatively low pressure drop; the provision of such a process which may be operated at a high average temperature for maximum reaction rate; the provision of such a process which operates at high average gas temperature without rapid degradation of catalyst; and the provision of such a process which allows a high average difference between reacting gas temperature and cooling fluid temperature for removal of reaction heat at a high rate.

Briefly, therefore, the present invention is directed to an improvement in a process for manufacture of maleic anhydride by passing through a tubular reactor a gas initially containing oxygen and a nonaromatic hydrocarbon having at least four carbon atoms in a straight chain. The tubular reactor contains a fixed bed of a catalyst comprising vanadium, phosphorus, and oxygen in which the hydrocarbon and oxygen react to produce maleic anhydride in the vapor phase, and the gas and catalyst bed are cooled during the reaction by transfer of heat to a cooling fluid through a wall of the tubular reactor. According to the improvement, the gas is passed in a single pass through a fixed catalyst bed in which the catalyst activity per unit volume of the bed varies with temperature and hydrocarbon concentration in the direction of flow of gas in such manner that the reaction rate is promoted by high activity in a region of low temperature and low hydrocarbon concentration within the bed and is restricted by relatively low activity in a critical region within the bed where the combination of temperature and hydrocarbon concentration could otherwise cause the reaction to proceed at an excessive rate or the gas temperature to rise excessively. The activity so varies in the direction of gas flow that the reactor can be operated at initial hydrocarbon concentrations of over 1.5% by volume, an integrated average temperature difference between gas and cooling fluid of at least about 15° C. over that portion of the bed in which the gas temperature exceeds the cooling fluid temperature, a hydrocarbon conversion of at least 70%, and a productivity of at least about 5.0 lbs. maleic anhydride per hour-ft$^3$ of catalyst, without the temperature difference between the gas and the cooling fluid exceeding 80° C. at any point in the catalyst bed during the course of the reaction. The rate of introduction of the hydrocarbon into the catalyst bed is controlled so that the conversion is at least about 70% and the temperature difference between the gas and the cooling fluid does not exceed about 80° C. anywhere within the catalyst bed, while the integrated average difference between the temperature of the reacting gas and the temperature of cooling fluid is at least about 15° C. over the portion of the bed in which the gas temperature exceeds the cooling fluid temperature.

The invention is directed to a further improvement in the aforesaid process in which a gas, initially containing oxygen, at least about 1.5% by volume hydrocarbon and a volatile phosphorus compound in a proportion sufficient to provide a phosphorus content of at least about $2 \times 10^{-5}\%$ by volume, is passed through a fixed catalyst bed. The activity of the bed varies with temperature and hydrocarbon concentration in the direction of flow of gas in such manner that the reaction rate is promoted by high activity in a region of low temperature and low hydrocarbon concentration within the bed and is restricted by relatively low activity in a critical region within the bed where the combination of temperature and hydrocarbon concentration could otherwise cause the reaction to proceed at an excessive rate or the gas temperature to rise excessively. The rate of introduction of the hydrocarbon into the catalyst bed is controlled so that the temperature difference between the gas and the cooling fluid does not exceed about 80° C. anywhere within the catalyst bed, while the integrated average difference between the temperature of the reacting gas and the temperature of cooling fluid is at least about 15° C. over the portion of the bed in which the gas temperature exceeds the cooling fluid temperature.

The invention is also directed to another improvement in the aforesaid process in which the gas is passed through a fixed catalyst bed in which the catalyst activity and gas permeability vary with the temperature and hydrocarbon concentration in the direction of gas flow. The activity of the bed varies with temperature and hydrocarbon concentration in the direction of flow of gas in such manner that the reaction rate is promoted by high activity in a region of low temperature and low hydrocarbon concentration within the bed and is restricted by relatively low activity in a critical region within the bed where the combination of temperature and hydrocarbon concentration could otherwise cause the reaction to proceed at an excessive rate or the gas temperature to rise excessively. The gas permeability varies in such manner that the pressure drop per unit distance in the direction of gas flow is lower in the critical region than in a downstream region between the critical region and the gas exit of the catalyst bed. A cooling load is applied by flowing a cooling fluid over the outside of the tubular reactor to remove heat generated in the reaction, and the rate of introduction of hydrocarbon into the catalyst bed is controlled so that the temperature difference between the gas and the cooling fluid does not exceed about 80° C. anywhere in the catalyst bed. The reaction is thereby controlled to synthesize maleic anhydride in high productivity and the rate of decay of activity of the catalyst is relatively low.

The invention is directed to a still further improvement in the aforesaid process in which the gas is passed through a fixed graded catalyst bed comprising a critical region that constitutes at least about 10% of the mass of the catalyst bed and is remote from the gas exit end of the bed, and a region downstream of the critical region with respect to the flow of gas. The catalyst bed in the critical region has a relatively low average surface to volume ratio and a relatively low activity, while the catalyst bed in the downstream region has a materially higher surface to volume ratio and a materially higher activity than the catalyst bed in the critical region. The hydrocarbon and oxygen are reacted in the bed to produce a gas containing maleic anhydride. A cooling load is applied to the outside of the tubular reactor to remove heat generated in the reaction. The rate of introduction of the hydrocarbon into the catalyst bed is controlled so that, when the gas temperature exceeds the cooling fluid by more than 30° C. anywhere in the catalyst bed, the highest temperature of the reacting gases is reached in the critical region or upstream of the critical region with respect to the direction of flow of gas, and the cooling fluid does not exceed 80° C. anywhere in the catalyst bed. The reaction is thereby controlled to synthesize maleic anhydride in high productivity and the rate of decay of activity of the catalyst is relatively low.

Other objects and features will be in part apparent and in part pointed out hereinafter.

DESCRIPTION OF THE PREFERRED EMBODIMENTS

Figure 1:
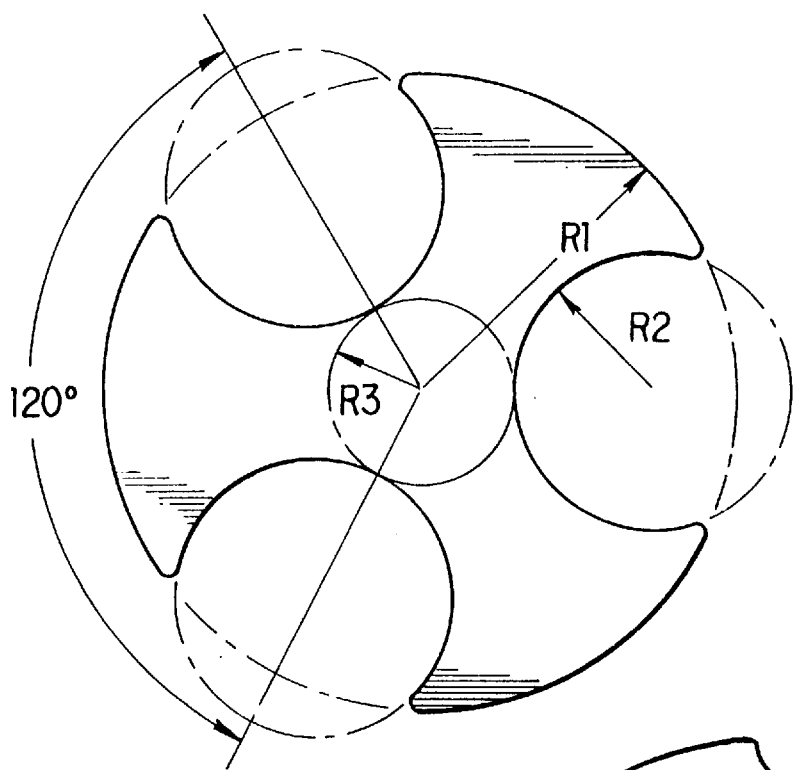
FIG. 1 is a cross-section of a catalyst body of the general type that is preferred for use in one or more of the regions of the catalyst bed in the process of the invention.

In accordance with the invention, a graded catalyst fixed bed reactor system is used for the catalytic oxidation of a hydrocarbon precursor of maleic anhydride, and the catalyst is graded in a manner which affords exceptionally high productivities, in excess of about 5.0, preferably at least about 5.5, more preferably at least about 6.0 lbs./ft³ catalyst-hour. By properly adapting the catalyst activity profile to the kinetics of the reaction and heat transfer capabilities of the reactor system, the hydrocarbon gas precursor may be introduced into the catalyst bed at high rate, and in concentrations exceeding 1.5% by volume, and the reaction carried out at a high average temperature and overall rate to produce maleic anhydride in good yield and selectivity. Despite the high average reaction temperature and reaction rate, the magnitude of the temperature peak at the hot spot is maintained at a moderate value.

The catalyst used in the process of the invention has the composition of a conventional mixed vanadium oxide and phosphorus oxide catalyst corresponding to the formula:

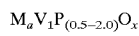

where:

M=a promoter metal a=0 to 0.2

V=vanadium

P=phosphorus x=sufficient to satisfy the valence state of M, V and P

Typical promoter metals include iron, lithium, chromium, hafnium, zirconium, lanthanum, uranium, cerium, copper, tellurium, tungsten, palladium, silver, manganese, zinc, molybdenum, rhenium, samarium, tantalum, thorium, cobalt, boron, silicon and tin.

As in a conventional process for the preparation of maleic anhydride, a feed gas containing n-butane or other suitable hydrocarbon reactant is passed through a tubular reactor containing a fixed bed of the catalyst in which the hydrocarbon and oxygen react to form maleic anhydride in the vapor phase. The starting material is a nonaromatic hydrocarbon having at least four carbon atoms in a straight chain. Preferred hydrocarbon reactants include n-butane, 1-butene, 2-butene and 1,3-butadiene. The reacting gas and the catalyst bed are cooled during the reaction by transfer of heat to a cooling fluid through the wall of the tubular reactor. Typically, the reactor is in the form of a shell and tube heat exchanger, with the catalyst pack contained within the tubes and the cooling fluid flowing through the shell and over the outsides of the tubes. In any case, the reactor tubes preferably have a high length to diameter ratio, preferably in the range of between about 50 and about 500, which promotes efficient heat transfer and provides for favorable reaction kinetics due to substantially plug flow of the reacting gases.

Because of plug flow operation, the reaction rate and temperature vary substantially through the tubular reactor. At the inlet the temperature is relatively low and the reaction rate correspondingly modest, despite high reactant concentrations. As the reaction progresses and the temperature rises, the reaction rate and consequent heat generation accelerate until the temperature reaches its maximum ("hot spot") at a point in the reactor, the location and magnitude of which is controlled by the profile of catalyst activity. Thereafter, the reaction rate declines as the gas stream becomes depleted in hydrocarbon reactant, and the temperature declines as the heat generation rate falls. Depending on overall catalyst activity, the reaction temperature may vary from 300° to 500° C., but is preferably in the range of 380° to 500° C., more preferably 410° to 470° C. In accordance with the invention, the catalyst activity per unit volume of the catalyst bed varies with temperature and hydrocarbon concentration in the direction of flow of gas in such manner that the reaction rate is promoted by high activity in a region of low temperature and hydrocarbon concentration within the catalyst bed, and is restricted by relatively low activity in a critical region within the bed where the combination of temperature and hydrocarbon concentration could otherwise cause the reaction to proceed at an excessive rate or the gas temperature to rise excessively. It will be understood that the term "restricted" means that the rate of reaction is less than it would be at high catalyst activity, even though the desired reaction is nonetheless being promoted to a significant degree by the activity that is present in the region in question. The activity varies in the direction of gas flow in such manner that the reactor can be operated at an initial hydrocarbon concentration of at least 1.5% by volume, an integrated average temperature difference between the gas and the cooling fluid of at least about 15° C. over the regions in which the gas temperature exceeds the salt bath temperature, a hydrocarbon conversion of at least about 70% in a single pass, and a productivity of at least about 5.0 lbs. maleic anhydride per hour-ft$^3$ of catalyst, without the temperature difference between the gas and the cooling fluid exceeding 80° C. at any point in the catalyst bed during the course of the reaction.

The rate of introduction of hydrocarbon into the catalyst bed is controlled so that the conversion of hydrocarbon is at least about 70% in a single pass, and the temperature differential between the gas and the cooling fluid does not exceed about 80° C. anywhere within the catalyst bed. The rate of hydrocarbon introduction is controlled by varying the initial concentration of hydrocarbon, the space velocity, or both. Preferably, the hydrocarbon content of the inlet gas is at least about 1.5% by volume, more preferably at least about 2.0%, more preferably at least about 2.2%. Space velocities are preferably in the range of between about 500 and about 4000 hr$^{-1}$, more preferably between about 1000 and about 3000 hr$^{-1}$. Since higher space velocities limit the maximum feasible $C_4$ concentration, and vice-versa, it is useful to consider the product of these two parameters, which product is defined herein as the gas loading factor. Preferably, the gas loading factor is at least about 3000 volume % $C_4$/hr., more preferably at least about 3500 volume % $C_4$/hr., most preferably at least about 4000 volume % $C_4$/hr. The pressure may range from about atmospheric to about 3.45×10$^2$ kPa gauge (50.0 psig), more preferably from about 1.24×10$^2$ to about 2.28×10$^2$ kPa gauge (18 to 33 psig). Inlet concentrations as high as 3.0% n-butane and productivities as high as 8.1 lbs. maleic anhydride/ft$^3$ catalyst-hour have been demonstrated to be feasible by properly adapting the catalyst activity profile to the reaction kinetics and heat transfer capabilities of a particular reactor system.

Where heat transfer capacity is substantial and the catalyst activity profile is optimally matched to the concentration profile in the reactor, the "hot spot" phenomenon may be almost entirely eliminated, thereby allowing the integrated average temperature differential between reacting gas and salt bath to be maximized. In such circumstances, optimal productivity may be realized at a temperature difference less than 30° C. However, in many commercial reactors, a level gas temperature is not practically feasible.

Whenever there is a hot spot in the reactor that exceeds the cooling fluid (salt bath) temperature by more than 30° C., the process conditions are preferably controlled so that the maximum temperature of the gas in the catalyst bed occurs before the gas leaves the aforesaid critical region, i.e., in the critical region or upstream of that region with respect to the direction of gas flow. Advantageously, the peak occurs in the critical region. Although consideration of second order effects may theoretically indicate that it can be acceptable, conceivably even advantageous in certain instances, to allow the temperature peak ($\geq$30° C. above the salt bath temperature) to be reached just past the end of the lowest activity region, an extra margin of protection against instability and runaway reaction is provided by matching catalyst activity profile and operating conditions to maintain the temperature peak within or upstream of the low activity critical region.

In accordance with the process, maleic anhydride is produced in high yield, and with higher productivity than has previously been considered feasible in a single pass operation where conversion exceeds 70%. A significant advantage of the process of the invention is its adaptability for operation with feed gas compositions that are within the flammability range at the reaction temperature. By thus allowing the use of relatively high initial hydrocarbon concentrations, and conversions in the 70+% range, such operation provides enhanced productivity. Thus, it is particularly preferred that the $C_4$ content of the feed gas be as high as possible; and in the process of the invention it has been found feasible to operate using a feed gas which is in the flammable range at the inlet of the catalyst bed. By control of the magnitude of the hot spot temperature through stratification (grading) of the catalyst, side reactions are minimized and sintering or other causes of catalyst decay are also inhibited. Thus, the process can be operated substantially continually over lengthy periods of time without significant decay in catalyst activity. More particularly, the maleic anhydride yield is stabilized so that average yield decay is less than 0.30% per month of the established initial maleic anhydride yield over an extended period of sustained operations.

Long term optimal performance is enhanced if, over a period of at least six months of substantially continual operation, the hot spot of the reaction is either eliminated or maintained within or upstream of the critical zone during at least 80% of any reactor operating time during which the temperature of the gas exceeds the temperature of the cooling fluid by more than 30° C. anywhere in the reactor. Typically, the life of a catalyst charge ranges from 2 to 5 years, in capacity operation more typically 2 to 3 years. Preferably, therefore, the hot spot of the reaction is maintained within or upstream of the critical zone at least about 80% of reactor operating time (during which the above noted 30° C. criterion is met) over a period of at least one year, and most preferably over at least 80% of the life of the catalyst bed. As a practical criterion, for reactors having a catalyst bed of greater than about 13 feet in length, the process is preferably controlled so that over a six months period, and over a one year period, and over at least 80% of the life of the catalyst, the location of the maximum temperature of gas in the catalyst bed is maintained at not greater than 45% of the length of the bed from the gas inlet for at least 80% of any operating time during which the gas temperature exceeds the salt bath temperature by more than 30° C.

Productivity is further promoted by a configuration in which the critical region is remote from the gas inlet end of the catalyst bed, and the activity in the critical region is lower than the average catalyst activity in either an upstream region between the inlet and the critical region or a downstream region between the critical region and the exit of the bed. The relatively high activity region between the inlet and the critical region promotes productivity by causing the entering gas to heat rapidly to reaction temperature. Moreover, it allows the critical region and the temperature peak that preferably occurs in the critical region to be located relatively near the inlet end of the reactor, while the low activity in the critical region prevents the peak from rising too high. Such a reaction profile promotes productivity by affording a substantial catalyst volume downstream of the temperature peak, and inhibits straying of the temperature peak toward the exit end of the reactor which, as discussed above, can lead to unstable operation.

In a preferred embodiment of the invention, the critical region is that region in which the concentration of hydrocarbon exceeds 0.8% by volume and the temperature would be more than 30° C. higher than the cooling fluid if catalyst activity throughout the bed were the same as in the region of high catalyst activity. Alternatively, the critical region is that region in which the temperature of said reacting gases would exceed 500° C. if the catalyst activity throughout the bed were the same as in regions of relatively high catalyst activity and the process were operated at a productivity of at least about 5.0 lbs. maleic anhydride/ft$^3$ catalyst-hour (80 kg/m$^3$ catalyst-hour) and a hydrocarbon content of at least about 1.5% in the inlet gas. The region encompassed by the first of these definitions is arbitrarily defined as critical region I, and that encompassed by the latter is defined as critical region II. In most operations, these regions are functionally equivalent, and their general location within the bed is generally the same, though the precise geometric boundaries of the critical region vary somewhat according to which definition is used. Both are contained within the "critical region" as used generically herein, which preferably constitutes at least about 10% of the total catalyst mass.

In any event, it is preferred that the catalyst activity in the critical region be materially lower, typically at least about 10% lower, more preferably at least about 15% lower, most preferably at least about 20% lower than the catalyst activity in the downstream region between the critical region and the gas exit from the bed. Advantageously, the catalyst activity of the critical region is at least about 10%, preferably at least about 15%, most preferably at least about 20%, lower than the average catalyst activity of the remainder of the bed. Where the temperature peak is not eliminated, the catalyst activity in the critical region is materially lower than the activity in regions of the bed, both upstream and downstream of the critical region, in which the concentration of hydrocarbon is less than about 0.5% by volume or the temperature difference between the gas and the cooling fluid would be less than 20° C. even if the catalyst activity throughout the bed were the same as the catalyst activity in the region of high catalyst activity.

As indicated, where discrete catalyst pellets or bodies are utilized, at least two types of catalyst are required to practice this invention, a catalyst that produces a low activity zone when charged to the reactor and a catalyst that provides a high activity zone when charged to the reactor. Note that there is no limitation to only two types of catalyst but at least two types are required to practice the invention. These catalysts are charged to the reactor with the low activity catalyst located in the first 75% of the reactor length in the direction of gas flow, measuring from the inlet. Two to ten zones of catalyst may be used, but commercial practicality generally limits the practice of the invention to three to four zones of catalyst. The different types of catalyst may have different forms of the same chemical composition, or they may be chemically distinct types of catalyst. All that is required is that the types of catalyst be distinguishable by a standardized catalyst actvity test, such as that described hereinbelow. As noted, the stratified catalyst charge may consist of a low activity zone followed by a high activity zone, or a low activity zone located between two higher activity zones.

Further in accordance with the invention, it has been discovered that the catalyst charge can be stratified (graded) in a manner which provides both low activity and low pressure drop in the critical region. Thus, for example, the coarseness of the catalyst may be varied to provide relatively coarse catalyst bodies of low geometric surface area to geometric volume ratio (hereinafter simply "surface to volume ratio") in the critical region, and finer catalyst bodies of higher surface to volume ratio in the remaining regions of the bed. The critical region containing coarse catalyst bodies has high gas permeability, while the other regions containing relatively fine catalyst bodies have a lesser gas permeability. By capitalizing on the association of both high gas permeability and low unit activity with low surface to volume ratio, and using the low surface to volume ratio catalyst in a region where reaction rate is at all events high despite lesser promotion from the catalyst, this preferred embodiment of the invention provides high productivity with relatively low overall pressure drop through the system.

It will be understood that the association between surface to volume ratio and either activity per unit bed volume or pressure drop varies with the shape of the catalyst body. Accordingly, in those instances where the configuration of catalyst bodies varies among regions in the bed, comparison can be made only with regard to measured activity and pressure drop. In an advantageous embodiment of the invention, the configuration of the catalyst bodies remains the same throughout the catalyst bed, but the bed is graded as to activity and pressure drop by variation in the size of the catalyst bodies. However, quite satisfactory systems may be provided in which catalyst body configuration varies substantially among regions of the bed. In any case, it is preferred that the constituent catalyst bodies of the various regions of the bed be so selected that, in the critical region, the pressure drop per unit distance in the direction of gas flow is materially lower than the pressure drop per unit distance in the bed as a whole.

Where the aspect ratio of the reactor tube is greater than 20 (L/D>20), the pressure drop of gas flowing through the tube may be accurately predicted from the relationship:

$$\Delta p = p_{in} - [p_{in}^2 - K_i T^{1.1} L^{2.76} (SV)^{1.76}]^{0.5}$$

where:
  $\Delta p$=gas pressure drop through the catalyst bed (or region thereof)
  $p_{in}$=reactor inlet pressure (to bed or region), psia
  $K_i$=a constant characteristic of the catalyst charge in region i of the bed (frictional constant)
  T=reactor cooling fluid temperature, °K
  L=length of the catalyst bed (or region thereof), ft.
  SV=space velocity, hr$^{-1}$
Thus, where:
  i=c=the critical region
  $K_c$=frictional constant for the critical
and where:
  i=t=the total bed
  $K_t$=frictional constant for the bed as a whole,
Preferably, the relationship between $K_c$ and $K_t$ is such that the pressure drop per unit distance in the direction of gas flow in the critical region is at least about 15% lower, more preferably at least about 20% lower, most preferably at least about 30% lower than in the remainder of the bed.

In the process of this embodiment, the rate of introduction of hydrocarbon is controlled, by controlling initial gas loading, so that temperature differential between the gas and the cooling fluid does not exceed about 80° C. at any point within the bed, and the average temperature difference between the reacting gas and the bed is at least about 15° C. over the region in which the gas temperature exceeds the salt bath temperature. The process is preferably operated using a single pass of gas through the reactor at a conversion of at least about 70%, but the process of this embodiment may also be operated with lower conversion and/or in a recycle system such as, for example, that described in Palmer U.S. Pat. No. 4,855,459. Where a single pass operation is used, the initial concentration of hydrocarbon in the gas entering the reactor is at least about 1.5%, preferably at least about 2.0%, most preferably at least about 2.2%, by volume. The rate of introduction of hydrocarbon, i.e. the gas loading factor, is controlled so that the temperature difference between the gas and the cooling fluid does not exceed about 80° C. anywhere in the catalyst bed, while the average temperature difference between the reacting gas and the cooling fluid is at least about 15° C. in the regions of the bed in which the gas temperature exceeds the salt bath temperature. Thus, in computing integrated average temperature difference for purposes of construing this criterion, the preheating portion of the reactor, in which salt bath temperature exceeds gas temperature, is ignored.

According to a still further alternative, the shape of the discrete catalyst bodies can be varied in the direction of gas flow in a manner which alters the surface to volume ratio of the bodies, even where all the catalyst bodies are of a given size or within a comparable size range. Generally, catalyst bodies having a shape that affords a relatively high surface to volume ratio exhibit a high activity and high pressure drop, while those with a low surface to volume ratio exhibit a relatively low activity and low pressure drop. However, such relationships do not necessarily prevail. Certain shapes specifically designed to provide high activity may exhibit lower pressure drop than other shapes of lower surface to volume ratio which are not as effective catalysts. The only essential characteristic of this embodiment of the invention is that discrete catalyst bodies of low activity occupy the critical region of the catalyst bed, that discrete catalyst bodies of another shape having relatively high activity occupy other regions of the bed, and that the frictional constant ($K_c$) for the catalyst bodies in the critical region be lower than the frictional constant for the catalyst bodies used in the other regions.

Although pressure drop characteristic varies predictably with surface to volume ratio only for catalyst bodies of the same shape, data has been developed for a variety of catalyst sizes and shapes which provides a basis for selection of the catalyst bodies to be used in the critical region and other regions of the catalyst bed. With reference to the equation:

$$\Delta p = p_{in} - [p_{in}^2 - K_i T^{1.1} L^{2.76} (SV)^{1.76}]^{0.5}$$

values for $K_i$ may be determined by charging the catalyst to a tube of the diameter of interest which has an aspect ratio of at least 100 and measuring the pressure drop at a variety of conditions and then fitting the data to the modified Ergun equation. Examples of actual measurements of $K_i$ are set forth below in Example 4 of this specification.

In the embodiment discussed above in which the critical region is remote from both the gas inlet and the gas exit of the bed, the gas permeability generally is higher in the critical region than in either the upstream region between the inlet and the critical region or the downstream region between the critical region and the gas exit. It is particularly preferred that the activity as a function of distance in the direction of gas flow be substantially inversely related to permeability as a function of distance in that direction, so that the pressure drop per unit distance is substantially directly related to the activity of the catalyst. The maintenance of such relationship throughout the bed allows overall pressure drop to be minimized while the catalyst activity profile is optimized.

Surprisingly, it has been discovered that an exceptional increase in productivity can be realized from the combined effects of a graded catalyst bed and the use of catalyst modifying compounds in the gas feed to the reactor. Gas phase organophosphorus compounds such as trimethyl phosphate are known to have a beneficial effect on the efficiency of fixed bed catalysts for the partial oxidation of hydrocarbons. The phosphorus compounds effectively retard the activity while increasing the selectivity of the catalyst during the early stages of the reaction in the region near the gas inlet, but are believed to be less effective in retarding the progress of the reaction in downstream regions where the gas has become relatively depleted of hydrocarbon content. Graded or stratified catalyst charge is adapted to achieve a similar effect. Although there would appear to be an element of redundancy, or at best an additive effect, from the use of both stratified charge and organophosphorus catalyst modifying compounds, it has been found that these two techniques work together synergistically to materially enhance productivity and yield.

In the various embodiments in which the catalyst is graded by surface to volume ratio, by catalyst shape, otherwise by relationship of pressure drop to activity, or by combined catalyst activity grading and use of catalyst modifying compound in the inlet gas, operation may utilize a single pass or a recycle system. Where a single pass operation is used, the feed gas to the reactor preferably contains at least about 1.5% by volume of hydrocarbon reactant, preferably 2.0%, most preferably 2.2% by volume. Space velocities are preferably in the range of between about 500 and about 4000 hr$^{-1}$, more preferably between about 1000 and about 3000 hr$^{-1}$. Preferably, the gas loading factor is at least about 3000 volume % $C_4$/hr., more preferably at least about 3500 volume % $C_4$/hr., most preferably at least about 4000 volume % $C_4$/hr. Where a catalyst modifying agent is used, the inlet gas should contain a volatile phosphorus compound in an proportion sufficient to provide a phosphorus content of at least about $2.0 \times 10^{-5}$% by volume, preferably between about $2.0 \times 10^{-5}$% and about $2.0 \times 10^{-3}$%. Suitable catalyst modifying compounds are generally described in U.S. Pat. No. 3,474,041, which is expressly incorporated herein by reference. Preferably, the catalyst modifying compound is a lower alkyl phosphate or lower alkyl phosphite, corresponding to the formulae:

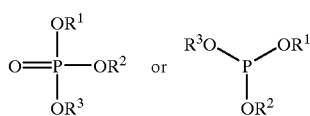

where $R^1$, $R^2$, and $R^3$ are hydrogen or $C_1$ to $C_6$ alkyl. At least one of $R^1$, $R^2$, and $R^3$ is alkyl. Preferred phosphorus compounds include trimethyl phosphate, triethyl phosphate, tri(n-butyl) phosphate, trimethyl phosphite and triethyl phosphite. Also suitable are compounds which correspond to the formulae:

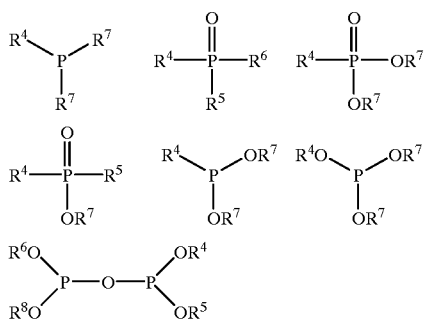

Where $R^4_1$ $R^5$, $R^6_1$ and $R^8$ are phenyl or alkyl substituents of 1 to 6 carbon atoms, and $R^7$ is selected from among $R^4$, $R^5$, $R^6$ and hydrogen. The rate of introduction of hydrocarbon into the catalyst bed is controlled so that the temperature differential between the gas and the cooling fluid does not exceed about 80° C. at any point within the bed, while the average temperature difference between the reacting gases and the cooling fluid is at least about 15° C. in the region downstream of the point where gas temperature and salt bath temperature crossover.

In accordance with the invention, activity of the catalyst may be determined by any standardized method which discriminates among catalysts according to their activity for conversion to maleic anhydride of n-butane or other non-aromatic hydrocarbon having at least four carbon atoms in a straight chain. A preferred method of classifying catalysts by activity is the activity test outlined below.

Figure 2:
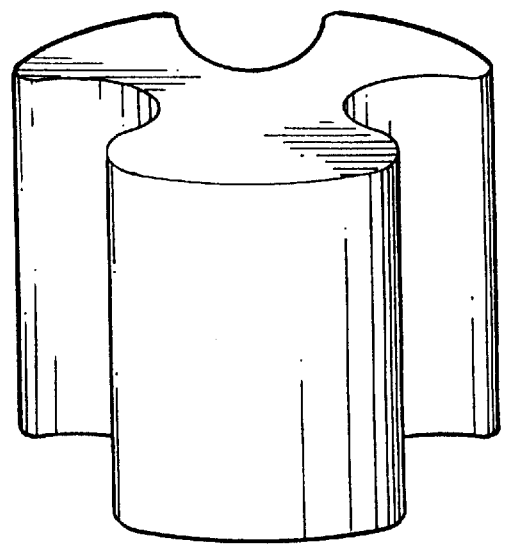
FIG. 2 is a perspective of a catalyst body designated "Trilobe," which is a species of the catalyst of FIG. 1.
Figure 3:
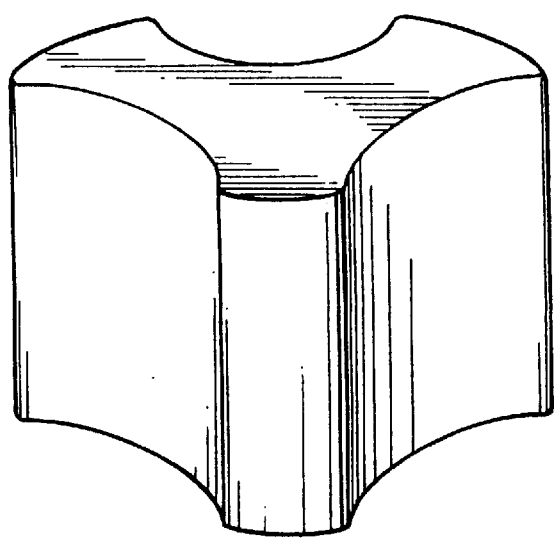
FIG. 3 is a perspective of a catalyst body designated "Tristar," which is another species of the catalyst body of FIG. 1.

Before describing the activity test, it should be noted that two of the catalysts tested, i.e., those catalysts identified in Table 2, infra, as Catalysts A and B, are cylinders which have the cross-sectional shape illustrated in FIG. 1. The grooves paralleling the axis of the cylinders create three lobes disposed 120° apart around the periphery of the cylinders. Where the radius $R_1$ is greater than the radius $R_2$, as is the case in catalysts A and B this form of catalyst is referred to as "Trilobe." A perspective of this form is shown in FIG. 2. Where $R_2 \geq R_1$, the catalyst form is referred to as "Tristar," and a perspective of this form of catalyst is illustrated in FIG. 3. Set forth in the table 1 below are the values for the radii $R_1$, $R_2$ and $R_3$ of the drawing by which the dimensions of the Trilobe and Tristar catalysts are defined.

TABLE 1

| TYPE | Tri-star | Trilobe | | | |
|---|---|---|---|---|---|
| | | II | III | IV | V |
| DIMENSIONS (INCHES) DIAMETER | 7/32 | 5/16 | 5/32 | 7/32 | 1/4 |
| $R_3$ | .0455 | .047 | .0294 | .0383 | .0375 |
| $R_2$ | .1094 | .0625 | .0325 | .0437 | .050 |
| $R_1$ | .1094 | .1563 | .0781 | .1094 | .125 |
| $R_2/R_1$ | 1.0 | .40 | .416 | .40 | .40 |
| $R_3/R_1$ | .42 | .30 | .38 | .35 | .30 |

NOTES:
1. The $R_2/R_1$ ratio measures the size of the cutting cylinder. As this number increases more volume is removed and more surface is exposed.
2. The $R_3/R_1$ ratio measures the depth of penetration of the cutting cylinder. As this number decreases more volume is removed and more surface is exposed.

The catalyst listed under "III" is referred to Trilobe III. Catalyst B of Table 2 has the size and shape of Trilobe III. The catalyst listed under "V" is Trilobe V. Catalyst A of Table 2 is a Trilobe V type catalyst. Note that Catalyst D is not of the Trilobe or Tristar type, but is rather an axially cored cylinder of annular cross-section.

Activity Test

The first step in the activity test is to determine the number of grams of catalysts to be charged to the activity testing reactor. This is done by first measuring the charge density of the catalyst to be tested in a reactor tube with a diameter equal to that of commercial reactors. This charge density is determined by dividing a known weight of catalyst by the volume it occupies in the reactor tube. This charge density, reported in grams/cm³ is multiplied by a standard volume, 17 cm³, to obtain the number of grams (+/-0.5 gms) to be charged to the ½" diameter by 12" long activity test reactor. A tube 21 mm in internal diameter and 502 mm in length (173.75 cc volume) is conveniently used to determine the charge densities.

The catalyst to be charged to the activity testing reactor must be in an activated state. It is not suitable to simply charge what is known in the literature as the precursor phase to the activity testing reactor. Several techniques are described in prior art to produce the activated catalyst. Some combination of calcination and/or reaction with butane is required to produce this active catalyst. A catalyst that is in a stable, activated state will be characterized by having a stable value for the % butane converted over 12 continuous hours on stream time in the activity test reactor. A stable % butane conversion value is one that changes less than 2 absolute percentage points over twelve continuous hours on stream. The activated catalyst is charged to the activity test reactor. The reactor is put in an uniform temperature fluidized sand bath and the sand bath is heated to 416+/-2° C. while $N_2$ is passed through the catalyst bed. When the fluidized sand bath has reached 416+/-2° C. a mixture of 1.5 mole % butane, 21 mole % oxygen and 77.5 mole % helium is passed through the catalyst bed at a flow rate of 566+/-25 sccm and a pressure of 10 psig. The catalyst is run at these conditions for at least 24 hours and the percent butane conversion at 416+/-2° C. is measured between 24 and 90 hours activity test reactor on stream time. This procedure produces a butane conversion % between 0 and 100%. Examples of the results of the above described charge density determination and activity test can be found in Table 2.

TABLE 2

| SAMPLE ID | DESCRIPTION | RUN NO. | CD G/CC | RX OST HOURS | RX WT GM | % CONV |
|---|---|---|---|---|---|---|
| Sample A | 6.35 mm D X 6.35 mm L — 3 grooves 45% solid cylinder | 4594793 | 0.56 | 24 | 9.45 | 60 |
| Sample B | 3.97 mm D X 3.97 mm L — 3 grooves 61% solid cylinder | 4566379 | 0.68 | 77 | 12 | 75.1 |
|  |  |  |  | 89 |  | 76.2 |
| Sample C | Spheres | 4594775 | 0.61 | 40 | 10.4 | 54.7 |
|  |  |  |  | 67 |  | 55.2 |
| Sample D | 6.35 mm X 6.35 mm cylinder with 2 mm core hole | 4594776 | 0.92 | 30.5 | 15.7 | 58.2 |
|  |  |  |  | 45.5 |  | 57.1 |

Determination of Stratification

To be considered to have a difference in activity for the purposes of stratification two catalysts must give different conversions by a minimum of three percentage points of conversion and preferably five percentage points of conversion. The maximum spread in conversion percentage points in a reactor should not be more than 75 percentage points and preferably not more than 50 percentage points. Two theoretical examples of stratification profiles constructed from four catalysts having the following conversion tests:

| Catalyst | % Conversion |
|---|---|
| W | 80 |
| X | 73 |
| Y | 67 |
| Z | 55 |

The two following stratification profiles both follow the general rule of having the low activity in the first 75% of the reactor but one is of the general type high/low/high activity and one is of the type low/high activity.

| Catalyst | Location | Catalyst | Location |
|---|---|---|---|
| Y | 0–25% | W | 0–10% |
| W | 25–100% | Z | 10–25% |
|  |  | Y | 25–40% |
|  |  | X | 40–50% |
|  |  | W | 50–100% |

Note that the location in the above table is measured from the reactor inlet with 0% signifying the reactor inlet and 100% the reactor exit.

Techniques For Producing Low Activity Catalyst

There are many ways to produce catalyst of low activity for the purposes of this invention. These are well known to those skilled in the art and will be described only by category here. The following is a partial list of techniques:

1. Chemical additives added to the catalyst either during or after the catalyst preparation procedure.
2. Catalysts of different shapes, sizes, and/or L/D ratios.
3. The preparation of a higher crush strength form, for example, a right circular cylinder tablet prepared to a side crush strength of 50 lbs, is less active than one prepared to 5 lbs side crush strength.
4. The addition of an inert powder to the active catalyst before forming such that each formed catalyst shape contains less active material than a shape made with 100% active powder.
5. Dilution of active catalyst forms with inert forms.
6. Coating the active catalyst particles with an inert coating either before or after forming.
7. Preparation of the catalyst by a different recipe.
8. Producing catalyst shapes that have internal dilution by coating an inert support with active catalyst.

The following examples illustrate the invention:

EXAMPLE 1

A twelve liter, round bottom flask, fitted with a paddle stirrer, a thermometer, a heating mantle and a reflux condenser was charged with isobutyl alcohol (9000 ml), oxalic acid (378.3 grams), and $V_2O_5$ (848.4 grams) to which was added $H_3PO_4$ (105.7%, 997.6 grams). The resulting mixture was then refluxed for about 16 hours to give a bright blue mixture. After stripping off ~2.25 liters of alcohol over 3 hours, the mixture was cooled, allowed to settle and the volume was reduced by 50% by decanting supernatant. The remaining material was quantitatively transferred to a flat porcelain dish and dried for 48 hours at 110° C. in nitrogen followed by 48 hours at 150° C. in air. The dried material was then transferred to another box oven where it was heated in air at 250–260° C. for approximately one hour to yield a grey-black catalyst precursor powder.

Using powder produced in the above fashion, various catalyst structures were formed using a Stokes 512 Rotary Tableting machine equipped with the needed dies and punches to produce the desired catalyst structure. To prepare tablet feed with the appropriate flow characteristics, the catalyst precursor powder was first blended to contain ~4 wt % graphite and then compressed on the machine into 1.27 cm cylinders with a tablet density of 1.30–1.50 gms/cc. The 1.27 cm slugs were then ground to produce a tablet feed powder in the 18–30 mesh size range. This powder was fed into the tablet machine equipped with the appropriate die and punches to produce the catalyst structure of interest. In forming the structures on the machine, the compaction pressure was adjusted to produce tablets with average side crushes of 13.3 to 89 N (3–20 lbs). The tablets produced are described in table 2, sample B and A.

Each of the catalyst structures was activated. The catalyst structure was placed into a 12"×12"×1" tray formed from stainless steel mesh screen having approximately 40% open area. They tray was transferred to an air purged box oven that had been heated to ~425° C. After holding at this temperature for approximately 1–2 hours, the tray of catalyst structures (bodies) was removed and cooled. Next the tray of catalyst structures was placed into a box oven purged with nitrogen gas and heated to approximately 275° C. at which point the atmosphere in the oven was changed to a mixture of ~50 volume percent nitrogen and 50 volume % steam. The temperature was raised over a period of ~1–2 hours to ~425° C. and held there for ~6 hours. The tray of catalyst structures was then allowed to cool to room temperature while purging the oven with dry nitrogen. The thusly prepared catalyst structures were charged to a 2.10 cm inside diameter×600 cm long fixed bed tubular reactor and butane oxidation reaction tested for several hundred hours.

The catalyst was then discharged and the catalyst forms were given the activity test described previously. The conversion reported for sample B was 75% and the conversion reported for sample A was ~60%. Detailed results from the charge density measurements and activity testing for these catalysts are reported in table 2.

Two catalyst packs were prepared from this catalyst. The first catalyst pack, example 1A, was not stratified and consisted of 574 cm of sample B. The second catalyst pack, example 1B, had the following stratification measured from the reactor inlet 45.7 cm sample B catalyst, followed by 157.5 cm of sample A catalyst, followed by 375.9 cm of sample B catalyst. Both catalyst packs were charged to a 2.10 cm inside diameter×600 cm long fixed bed tubular reactor.

Both catalysts were brought on stream at low butane concentration and increased to 2.0 mole % butane feed with in the first 12 hours. Important test parameters, GHSV= 1600–1650 Hr$^{-1}$ inlet pressure=29–31 psig and feed stream moisture=2.2–2.6 mole %, were the same for both tests. The butane concentration was increased in steps of 0.1 mole % about every ~12–24 hours until a significant yield decline or a large hot spot increase was observed. The results of these tests are summarized in table 3 below:

TABLE 3

| Catalyst | Hours | % Butane | BathT | H Spot | % Conv. | % Yield | Prod. |
|---|---|---|---|---|---|---|---|
| Ex 1A | 10 | 2.0 | 404 | 437 | 81.4 | 59.2 | 4.95 |
| Ex. 1B | 12 | 2.0 | 404 | 430 | 79.5 | 57.5 | 4.89 |
| Ex 1A | 41 | 2.1 | 401 | 488 | 80.4 | 53.8 | 4.74 |
| Ex 1B | 28.5 | 2.1 | 407 | 442 | 79.5 | 57.0 | 5.05 |
| Ex 1A | | 2.2 | HOT | SPOT | RUN | AWAY | |
| Ex 1B | 46.5 | 2.2 | 408 | 458 | 80.5 | 56.5 | 5.20 |

EXAMPLE 2

The catalyst was prepared in a manufacturing plant substantially according to the following laboratory recipe. A twelve liter, round bottom flask, fitted with a paddle stirrer, a thermometer, a heating mantle, a reflux condenser, a gas dispersion tube and a Dean Stark trap was charged with isobutyl alcohol (8300 ml) and cooled to 10–15° C. To the alcohol was added a room temperature solution of 85.5% H$_3$PO$_4$ (901.8 grams) and P$_2$O$_5$ (343.4 grams). While maintaining the temperature of 5–10° C., V$_2$O$_5$ (963 grams), LiCl (1.35 grams) and iron powder (0.96 grams), and an additional 1.0 liter of isobutyl alcohol are added. To the stirred mixture, dry HCl gas (2037 grams) was added through a gas dispersion tube over a period of 4.67 hours while maintaining the reaction mixture between 40–50° C. The resulting solution was refluxed for ~2 hours, then the alcohol was stripped (5.4 liters of alcohol removed) over a period of 5 hours, followed by an additional 1.38 hour reflux, followed by a removal of an additional 1.5 liter of distillate over a 2.36 hour period. The mixture was cooled and quantitatively transferred to a porcelain dish and dried at 150° C. for about 5.5 hours. The dried material was then transferred to another box oven where it was heated in nitrogen at 250–260° C. for approximately three hours, followed by gradual replacement of nitrogen by air heating an additional three hours to yield a grey-black catalyst precursor powder.

This black catalyst precursor powder was spheroidized using a 20" diameter pan pelletizer. The spheres produced ranged in size from 4.0 mm to 8.0 mm in diameter and had the following size distribution.

| SIZE RANGE | PERCENT IN RANGE |
|---|---|
| +8.0 MM | 0.0% |
| –8.0 MM, +6.7 MM | 27.4% |
| –6.7 MM, +4.8 MM | 66.4% |
| –4.8 MM | 6.2% |

The catalyst was activated in a multi-tube plant reactor substantially according to the following procedure. The prepared catalyst structures were charged to a commercial reactor having multiple tubes 2.10 cm inside diameter×335.3 cm long, and the reactor was slowly warmed to 400° C. (between 300° C. and 400° C. at 1° C./hr) while passing a gas stream containing 0.6 mol per cent n-butane in air over the catalyst beginning at about 280° C. The so conditioned catalyst was then run in a butane oxidation reaction for ~3000 hours and discharged. The fully equilibrated spheroidized catalyst, sample C, was tested using the activity test described previously. The conversion obtained in the activity test was ~55%, details are given in table 2.

A catalyst pack for large tube testing was prepared from this catalyst and the sample B catalyst. This catalyst pack had the following stratification measured from the reactor inlet 30.4 cm of sample B, followed by 152.4 cm of sample C, followed by 396.2 cm of sample B. The catalyst pack prepared as described above was charged to a 2.10 cm inside diameter×600 cm long fixed bed tubular reactor.

The catalyst was brought on stream at low butane concentration and increased to 2.0 mole % butane feed with in the first 24 hours. Important test parameters were GHSV= 1600–1650 Hr$^{-1}$, inlet pressure=29–31 psig and feed stream moisture=2.2–2.6 mole %. The butane concentration was increased in steps of 0.1 mole % periodically until a significant yield decline or a large hot spot increase was observed. The results of these tests are summarized in table 4 below:

TABLE 4

| Catalyst | Hours | % Butane | BathT | H Spot | % Conv. | % Yield | Prod. |
|---|---|---|---|---|---|---|---|
| Ex 1A | 10 | 2.0 | 404 | 437 | 81.4 | 59.2 | 4.95 |
| Ex 2 | 21 | 2.0 | 403 | 434 | 78.7 | 59.9 | 5.01 |
| Ex 1A | 41 | 2.1 | 401 | 488 | 80.4 | 53.8 | 4.74 |
| Ex 2 | 38 | 2.1 | 405 | 443 | 80.1 | 59.2 | 5.20 |
| Ex 1A | | 2.2 | HOT | SPOT | RUN | AWAY | |
| Ex 2 | 64 | 2.2 | 406 | 448 | 80.2 | 58.5 | 5.38 |
| Ex 2 | 119 | 2.34 | 406 | — | 79.5 | 54.6 | 5.39 |

EXAMPLE 3

Catalysts from two different recipes are involved in the testing for this example. The recipe from Example 1 was used to prepare the catalyst, sample B, used in the most active portions of the reactor. The catalyst, sample D, used in the low activity zone was prepared using the recipe below.

Recipe Catalyst Sample D

A twelve liter, round bottom flask, fitted with a paddle stirrer, a thermometer, a heating mantle and a reflux condenser was charged with 9000 ml of isobutyl alcohol, 378.3 grams of oxalic acid, and 848.4 grams of $V_2O_5$ to which was added 997.6 grams of $H_3PO_4$ (105.7%). The resulting mixture was then refluxed for about 16 hours to give a bright blue mixture. After stripping off 6 liters of alcohol over 3 hours, the mixture was cooled and quantitatively transferred to a flat porcelain dish and dried for 48 hours at 110° C. in nitrogen followed by 48 hours at 150° C. in air. The dried material was then transferred to another box oven where it was heated in air at 250–260° C. for approximately one hour to yield a grey-black catalyst precursor powder.

Using powder produced in the above fashion cored cylinders were formed using a Stokes 512 Rotary Tableting machine. To prepare tablet feed the catalyst precursor powder was first blended with 316 stainless steel powder and graphite powder to a composition of 25% 316 stainless steel, 4% graphite and 71% catalyst precursor powder and then compressed on the machine into 1.27 cm cylinders with a tablet density of 1.75–1.95 gms/cc. The 1.27 cm slugs were then ground to produce a tablet feed powder in the 18–30 mesh size range. This powder was fed into the tablet machine equipped with the appropriate die and punches to produce the catalyst structure of interest. In forming the cored cylinders on the machine, the compaction pressure was adjusted to produce tablets with average side crushes of 13.3 to 89 N (3–20 lbs).

The catalyst was activated by the following procedure. The cored cylinders were placed into a 12"×12"×1" tray formed from stainless steel mesh screen having approximately 40% open area. The tray was transferred to an air purged box oven that had been heated to ~425° C. After holding at this temperature for approximately 1–2 hours, the tray of cored cylinders was removed and cooled. Next the tray of catalyst was placed into a box oven purged with nitrogen gas and heated to approximately 275° C. at which point the atmosphere in the oven was changed to a mixture of ~50 volume percent nitrogen and 50 volume % steam. The temperature was raised over a period of ~1–2 hours to ~425° C. and held there for ~6 hours. The tray of cored cylinders was then allowed to cool to room temperature while purging the oven with dry nitrogen. The thusly prepared catalyst was charged to a 2.10 cm inside diameter×600 cm long fixed bed tubular reactor and performance tested in the butane oxidation reaction.

This catalyst, sample D, was discharged and subjected to activity testing. The activity from the testing was ~58%. Detailed results from this testing can be seen in table 2.

A catalyst pack for large tube testing was prepared from this catalyst, sample D, and the sample B catalyst. This catalyst pack had the following stratification measured from the reactor inlet: 30.4 cm of sample B, followed by 152.4 cm of sample D, followed by 396.2 cm of sample B. The catalyst pack prepared as described above was charged to a 2.10 cm inside diameter×600 cm long fixed bed tubular reactor.

The catalyst was brought on stream at low butane concentration and increased to 2.0 mole % butane feed within the first 24 hours. Important test parameters were GHSV= 1600 $Hr^{-1}$, inlet pressure=29–31 psig and feed stream moisture=2.2–2.6 mole %. The butane concentration was increased in steps of 0.1 mole % periodically until a significant yield decline or a large hot spot increase was observed. The results of these tests are summarized in table 5 below:

TABLE 5

| Catalyst | Hours | % Butane | BathT | H Spot | % Conv. | % Yield | Prod. |
|---|---|---|---|---|---|---|---|
| Ex 1A | 10 | 2.0 | 404 | 437 | 81.4 | 59.2 | 4.95 |
| Ex 3 | 17 | 2.0 | 415 | 427 | 61.8 | 55.3 | 4.55 |
| Ex 1A | 41 | 2.1 | 401 | 488 | 80.4 | 53.8 | 4.74 |
| Ex 3 | 31 | 2.1 | 419 | 433 | 79.3 | 56.3 | 4.98 |
| Ex 1A | | 2.2 | HOT | SPOT | RUN | AWAY | |
| Ex 3 | 89 | 2.2 | 416 | 434 | 80.3 | 56.7 | 5.21 |
| Ex 3 | 113 | 2.3 | 418 | 437 | 80.5 | 55.9 | 5.4 |
| Ex 3 | 123 | 2.4 | 418 | 438 | 79.2 | 55.4 | 5.56 |
| Ex 3 | 234 | 2.5 | 419 | 450 | 81.8 | 54.7 | 5.73 |
| Ex 3 | 267 | 2.6 | 419 | 453 | 81.2 | 52.8 | 5.77 |
| Ex 3 | 302 | 2.7 | 419 | 481 | 81.1 | 49.9 | 5.64 |

Note: Operation unstable at 2.7% butane in example 3

EXAMPLE 3B

Catalytic oxidation of n-butane to maleic anhydride was conducted using the procedure generally described in Example 3, but the catalyst bed contained only two zone of differing activity. The first zone was 64" in length and contained ¼" cored cylinders (Sample D of Table 2) and the second zone was 164" in length and contained 5⁄32" Trilobes (Sample B of Table 2).

The reactor at 148 hours of operation and n-butane feed concentration of 2.6% by volume, had an average salt bath temperature was 414° C., the hot spot temperature was 472° C., the conversion was 79.9%, the molar yield was 53.1% and the productivity was 5.77 lbs./ft³ catalyst-hour (92.8 kg/m³ catalyst-hour).

EXAMPLE 4

Using the method described hereinabove $K_i$ values were determined for various sizes and shapes of catalyst. The values of $K_i$ for use in the equation:

$$\Delta p = p_{in} - [p_{in}^2 - K_i T^{1.1} L^{2.76} (SV)^{1.76}]^{0.5}$$

were found to be as set forth in table 6 below:

TABLE 6

| Solid Shape | $K_i$ Value |
|---|---|
| Trilobe III | $8.72 \times 10^{-10}$ |
| Trilobe V | $4.10 \times 10^{-10}$ |
| 3/16" cored tablets | $10.1 \times 10^{-10}$ |
| 7/32" cored tablets | $5.49 \times 10^{-10}$ |
| 1/4" cored tablets | $4.53 \times 10^{-10}$ |
| 6 mm inert spheres | $3.95 \times 10^{-10}$ |
| 8 mm inert spheres | $3.51 \times 10^{-10}$ |
| 1/8" solid tabs | $15.3 \times 10^{-10}$ |
| Tristars | $8.14 \times 10^{-10}$ |
| Tristars + 10% (vol) 6 mm inert | $7.97 \times 10^{-10}$ |
| Tristars + 20% (vol) 6 mm inert spheres 4–8 mm | $7.76 \times 10^{-10}$ |
| | $5.66 \times 10^{-10}$ |
| rings 8 × 8 × 4 mm | $3.09 \times 10^{-10}$ |

For purposes of comparison, the surface to volume ratios of a number of these catalysts were determined. These determinations were based on the ratio of the geometric surface area to the geometric volume enclosed by the surface, and do not include any effects of porosity. The results are set forth in Table 7 below

TABLE 7

| Solid Shape | S/V cm$^{-1}$ |
|---|---|
| Trilobe III | 27 |
| Trilobe V | 21 |
| 3/16" cored tablets | 17 |
| 7/32" cored tablets | 14 |
| 1/4" cored tablets | 12 |
| 6 mm inert spheres | 10 |
| 8 mm inert spheres | 7.5 |
| 1/8" solid tabs | 17 |
| 3/16" solid tabs | 13 |
| spheres 4–8 mm | avg. ~ 10 |

These measurements demonstrate that, while surface to volume ratio is correlatable with pressure drop for catalyst bodies of a given shape, empirical determinations must be made to compare the pressure drop characteristics of catalyst bodies of different shapes. However, such determinations are readily made by routine experimentation. Accordingly, one skilled in the art can readily apply the principles described herein to establish an appropriate catalyst profile for high productivity and low pressure drop.

From Table 6, it may be seen that a stratified charge can be produced from Tristars by dilution in the critical region with inert spheres. Thus, the entire bed may be constituted of Tristar active catalyst of a single size and activity, while a critical region of both low activity and low pressure drop is provided by simply diluting the Tristar catalyst in that region with inert spheres.

EXAMPLE 5

The tubes of a plant scale shell and tube type reactor were packed with two different catalysts, having the sizes and shapes described above as Trilobe III and Trilobe V, to provide a first region containing Trilobe III, a second, critical region containing Trilobe V, and a third region containing Trilobe III. The composition of the catalyst corresponded to the formula:

$$M_a V_1 P_{(1.08)} O_x$$

where:

M=a promoter metal a=zero

V vanadium

P=phosphorus x=sufficient to satisfy the valence state of V and P

The catalyst was prepared at a plant scale substantially in accordance with the laboratory procedure described below.

A twelve liter, round bottom flask, fitted with a paddle stirrer, a thermometer, a heating mantle and a reflux condensor was charged with isobutyl alcohol (9000 ml), oxalic acid (378.3 grams), and $V_2O_5$ (848.4 grams) to which was added $H_3PO_4$ (105.7%, 997.6 grams ). The resulting mixture was then refluxed for about 16 hours to give a bright blue mixture. After stripping off ~2.25 liters of alcohol over 3 hours, the mixture was cooled, allowed to settle and the volume was reduced by 50% by decanting supernatant. The remaining material was quantitatively transferred to a flat porcelain dish and dried for 48 hours at 110° C. in nitrogen followed by 48 hours at 150° C. in air. The dried material was then transferred to another box oven where it was heated in air at 250–260° C. for approximately one hour to yield a grey-black catalyst precursor powder.

Using powder produced in the above fashion, various catalyst structures were formed using a Stokes 512 Rotary Tableting machine equipped with the needed dies and punches to produce the desired catalyst structure. To prepare tablet feed with the appropriate flow characteristics, the catalyst precursor powder was first blended to contain ~4 wt % graphite and then compressed on the machine into 1.27 cm cylinders with a tablet density of 1.30–1.50 gms/cc. The 1.27 cm slugs were then ground to produce a tablet feed powder in the 18–30 mesh size range. This powder was fed into the tablet machine equipped with the appropriate die and punches to produce the catalyst structure of interest. In forming the structures on the machine, the compaction pressure was adjusted to produce tablets with average side crushes of 13.3 to 89 N (3–20 lbs). The tablets produced are described in table 2, sample B and A.

Each of the catalyst structures was activated. The catalyst precursor bodies were placed onto a 30.48 cm×30.48×2.54 cm tray formed from stainless steel mesh screen having approximately 40% open area stainless steel and placed in a box oven. The bodies were heated from room temperature (approximately 25° C.) to 275° C. in air. The temperature was thereafter increased to 425° C. at a programmed rate of 4° C./min in about 50 mol % air/50 mol % steam. The temperature was maintained at 425° C. for a period of 1 hour, and thereafter in an atmosphere of 50 mol % steam/50 mol % nitrogen for a period of 6 hours.

The maleic anhydride reactor tubes were packed with catalyst to a bed length of 228". The first region was about 30" in length, the second about 60", the third about 138". Experimental reactions have been conducted in this reactor in a manufacturing plant for a period of 12 months. A reactant gas containing between about 1.5% and about 2.5% by volume n-butane, about $3.1\times10^{-4}\%$ phosphorus as trimethylphosphate, and approximately 20% by volume oxygen (from ambient air) was fed to the reactor and the n-butane catalytically oxidized to produce maleic anhydride. Operation was single pass and conversions of n-butane ranged from about 79% to about 90%. Space velocities were maintained in the range of about 1150 hr$^{-1}$ to about 1650 hr$^{-1}$, and the inlet n-butane concentration was controlled so that the temperature of the hot spot in the reactor did not exceed the temperature of the salt bath by more than about 60° C. at any point in the reactor.

The performance of the reactor was monitored, temperature profiles were observed and data taken on yield, productivity, conversion, pressure drop and butane content of the feed. The results are set forth in Table 8 at four months operation and at an n-butane concentration of ~2.4% by volume (97% purity) and a space velocity of about 1625 hr$^{-1}$, and for ten months at an n-butane concentration of ~2.1% by volume (97% purity) and a space velocity of about 1616 hr$^{-1}$:

TABLE 8

|  | 4 mos. | 10 mos. |
|---|---|---|
| Yield | 56% | 58% |
| Productivity | 5.65 lbs.MA/ft$^3$-hr | 5.13 lbs.MA/ft$^3$-hr |
| Conversion | 83% | 86% |
| Salt Bath Temp. | 420° C. | 426° C. |
| Hot Spot Temp. | 460° C. | 454° C. |
| Hot Spot Location | 2nd zone | 2nd zone |
| Pressure Drop | 15 psi | 15 psi |

Observation of the temperature profile indicated that, over a period longer than six months, the hot spot of the reactor was established and maintained within or upstream of the critical region nearly 100% of the time during which the gas temperature exceeded the cooling fluid by more than 30° C. anywhere in the reactor.

As indicated by the results of this example, the catalyst loading schedule for 13–25 ft. long reactors having the performance characteristics of the reactor of this example is preferably as set forth below, the activity of the highest activity catalyst region being taken as 1.0:

| Region of Bed | % Reactor length of Region | Catalyst Activity |
| --- | --- | --- |
| inlet through critical | 15–45% | 0.7–0.9 |
| downstream | 45–85% | 1.0 | and, separating the pre-heat from the critical region in a three region reactor:

| Region of Bed | % Reactor length of Region | Catalyst Activity |
| --- | --- | --- |
| pre-heat | 8–22% | 0.8–1.0 |
| critical | 10–30% | 0.6–0.9 |
| downstream | 48–82% | 1.0 |

EXAMPLE 6

A pilot plant shell and tube reactor was packed with Trilobe III and Trilobe V catalyst, each catalyst being prepared in the manner described in Example 5. The reactor was also operated in a manner comparable to that described in Example 5. However, the tube was packed in the following sequence:—1"—inerts (6 mm alumina); 35"—Trilobe III; 36"—Trilobe V; 150.5"—Trilobe III. Operation was conducted at a variety of experimental conditions over a period of ~2000 hours.

A reactant gas containing between about 1.5% and about 2.4% n-butane, about $3.1 \times 10^{-4}$% by volume phosphorus as trimethyl phosphate was fed to the reactor. Conversions of n-butane ranged from 75% to about 90% and the space velocity was maintained between about 1500 and about 2650 hr$^{-1}$. The gas loading was controlled so that the difference between the temperature of the gas at the hot spot and the temperature of the salt bath did not exceed about 60° C.

The performance of the reactor was monitored, temperature profiles were observed and data taken on yield, productivity, conversion, pressure drop and n-butane content of the feed. The results set forth in Table 9 were obtained at 587 hours operation and at 2.21% by volume n-butane, 2630 GHSV, and $3.1 \times 10^{-4}$ volume % P as trimethyl phosphate:

TABLE 9

| Yield | 54% | |
| --- | --- | --- |
| Productivity | 8.10 | lbs.MA / ft$^3$-hr |
| Conversion | 82% | |
| Salt Bath Temp. | 423° C. | |
| Hot Spot Temp. | 467° C. | |
| Hot Spot Location | 37.4" | |
| Pressure Drop | 28 psi | |

Observation of the temperature profile indicated that the hot spot of the reactor was established and maintained within or upstream of the critical region nearly 100% of the time during periods of high productivity in which the temperature of the gas exceeded the temperature of the cooling fluid by more than 30° C. anywhere in the reactor.

EXAMPLE 7

Maleic anhydride was produced by catalytic oxidation of n-butane in a laboratory reactor using both unstratified and stratified reactor charges. In certain runs, the feed gas included trimethyl phosphate (TMP), while in other runs no catalyst modifying compound was included in the feed. After steady state operation was established at an n-butane concentration of 2.0% by volume, the n-butane content was increased in small increments periodically until a maximum productivity was reached. Set forth in Table 10 are the catalyst loadings schedules, TMP content of the feed gas, the n-butane content at maximum productivity and the highest productivity achieved. Exemplary catalyst runs 1A, 1B, and 2 from Examples 1 and 2 are set forth for purposes of comparison.

TABLE 10

| Catalyst | Run No. | n-Butane % at Max. Productivity | Highest Productivity |
| --- | --- | --- | --- |
| 100% Trilobe 5/32" (Example 1A) | C2725 | 2.10% 0 PPM TMP* | 5.05 |
| | C2737 | 2.13% 3 ppm TMP | 5.05 |
| | | 2.50% 6 ppm TMP | 5.57 |
| 2–20" 5/32" Trilobes 20–82" 1/4" Trilobes 82–230" 5/32" Trilobes (Example 1B) | C2726 | 2.2% 0 ppm TMP | 5.20 |
| | | 2.4% 1.6 ppm TMP | 5.33 |
| | | 2.3% 1.6 ppm TMP | 5.37 |
| 2–14" 5/32" Trilobes 14–74" Spheres 74–230" 5/32" Trilobes (Example 2) | C2735 | 2.33% 0 ppm TMP | 5.52 |
| | | 2.74% 3 ppm TMP | 6.46 |
| | | 2.81% 6 ppm TMP | 6.47 |

*by weight TMP

As compared to unstratified 5/32" Trilobes, the n-butane concentration at maximum productivity is increased from 2.1% to 2.2% (0.1%) by stratification with a critical region containing 1/4" Trilobes (Table 3). The n-butane concentration at maximum productivity is essentially not increased (0.0%) by adding 3 ppm TMP without stratification, and is increased to 2.5% (0.4% difference) by adding 6 ppm TMP without stratification.

However, the combination of 1.6 ppm TMP and stratification with 1/4" Trilobes increases the maximum butane feed concentration to 2.4% (0.3% difference from the base case), which can be seen to exceed the additive effect of stratification alone and 3 ppm TMP alone (0.1%+0.0%=0.1%).

Stratification of a 5/32" Trilobe bed by using a critical region containing sample C spheres increases the maximum butane feed concentration to 2.33% (0.23% difference) while the combination of this form of stratification with 3 ppm TMP in the feed increases the maximum butane feed concentration to 2.74% (0.64% difference) which exceeds the sum of the effects of stratification and 3 ppm TMP (0.23%+0.0%=0.23%). Similarly, the combination of this form of stratification and 6 ppm TMP increases the maximum butane feed concentration to 2.81% (0.71% difference) which exceeds the additive effect of the stratification and 6 ppm TMP (0.23%+0.4%=0.63%).

EXAMPLE 8

The tubes of a pilot plant shell and tube type reactor were packed with Trilobe III and Trilobe V, to provide first region containing Trilobe III, a second, critical region containing Trilobe V, and a third region containing Trilobe III. The composition of the catalyst corresponded to the formula:

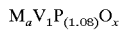

$M_a V_1 P_{(1.08)} O_x$ where M, a, V, P and x are as defined above. The catalyst was prepared as described in Example 5.

The reaction tubes were packed with catalyst to a bed length of 228". The inlet section of the catalyst bed was packed with 1" of inert bodies. Thereafter, the first catalyst region was 48" in length, the second 60", and the third 120". The reactant gas contained between about 1.5% and about 2.4% by volume n-butane and approximately 20% by volume oxygen (from ambient air). Operation was single pass and conversions of n-butane ranged from about 79% to about 90%. Space velocities were maintained in the range of about $1150hr^{-1}$ to about $1650hr^{-1}$, and the inlet n-butane concentration was controlled so that the temperature of the hot spot in the reactor did not exceed the temperature of the salt bath by more than about 60° C. at any point in the reactor.

The performance of the reactor was monitored, temperature profiles are observed and data are taken on yield, productivity, conversion, pressure drop and butane content of the feed. The results of this example (C2770), as set forth in Table 11, were obtained at 2516 hours operation and at an n-butane concentration of 2.40% by volume, and a phosphorus concentration of $5 \times 10^{-4}$ volume % in the form of trimethyl phosphate, and 1625 GHSV:

TABLE 11

| | |
|---|---|
| Yield | 58% |
| Productivity | 5.88 lbs.MA/ft³-hr |
| Conversion | 82% |
| Salt Bath Temp. | 425° C. |
| Hot Spot Temp. | 454° C. |
| Hot Spot Location | 37.4" |
| Pressure Drop | 14 psi |

This embodiment is expected to provide near optimum performance for the reactor in question. For reactor systems of comparable performance characteristics, therefore, a preferred catalyst loading schedule is the following, using defining the activity of the most active catalyst region as 1.0:

| Region of Bed | % Reactor length of Region | Catalyst Activity |
|---|---|---|
| pre-heat | 15–25% | 0.9–1.0 |
| critical | 15–30% | 0.7–0.9 |
| downstream | 48–56% | 1.0 |

A more preferred catalyst loading schedule is as follows:

| Region of Bed | % Reactor length of Region | Catalyst Activity |
|---|---|---|
| pre-heat | 19–23% | 0.9–1.0 |
| critical | 23–29% | 0.7–0.9 |
| downstream | 48–56 | 1.0 |

As various changes can be made in the processes of this invention without departing from the scope of the invention, it is intended that all matter contained in the above description shall be interpreted as illustrative and not in a limiting sense.

What is claimed is:

1. In a process for the manufacture of maleic anhydride by passing through a tubular reactor a gas initially containing oxygen and a nonaromatic hydrocarbon having a least four carbon atoms in a straight chain, said tubular reactor containing a fixed bed of a catalyst comprising vanadium, phosphorus and oxygen in which the hydrocarbon and oxygen react to produce maleic anhydride in the vapor phase, said gas and catalyst bed being cooled during the reaction by transfer of heat to a cooling fluid through a wall of said tubular reactor, the improvement which comprises:

passing a gas through a fixed catalyst bed, said gas initially containing oxygen, at least about 1.5% by volume of said hydrocarbon and a volatile phosphorus compound in a proportion sufficient to provide a phosphorus content of at least about $2 \times 10^{-5}$% by volume, the catalyst activity per unit volume of said fixed catalyst bed varying with temperature and hydrocarbon concentration in the direction of flow of gas in such manner that the reaction rate is promoted by high activity in a region of low temperature and low hydrocarbon concentration within the bed and is restricted by relatively low activity in a critical region within the bed where the combination of temperature and hydrocarbon concentration could otherwise cause the reaction to proceed at an excessive rate or the gas temperature to rise excessively; and controlling the rate of introduction of said hydrocarbon into the catalyst bed and the temperature of the reaction so that the conversion of said hydrocarbon is at least about 79%, temperature differential between said gas and said cooling fluid does not exceed about 80° C. at any point within said bed while the integrated average temperature difference between the reacting gas and the cooling fluid is at least about 15° C. over the portion of the bed in which the gas temperature exceeds the cooling fluid temperature.

2. An improved process as set forth in claim 1 wherein said phosphorus compound comprises an organophosphorus compound.

3. An improved process as set forth in claim 2 wherein said gas initially contains said phosphorus compound in a proportion sufficient that the phosphorus content of the gas is between about $2 \times 10^{-5}$% and about $2 \times 10^{-3}$% by volume.

4. An improved process as set forth in claim 1 wherein said critical region comprises a region in which the hydrocarbon concentration exceeds 0.8% by volume and the gas temperature would be more than 30° C. higher than the cooling fluid temperature if the catalyst activity throughout the bed were the same as in said region of high catalyst activity.

5. An improved process as set forth in claim 1 wherein the conditions of the process are controlled so that, during a period of at least six months of substantially continual operation, the location of the maximum temperature of said gas in said catalyst bed is maintained within said critical region or upstream of said critical region with respect to the direction of gas flow at least 80% of any time during which the temperature of the gas exceeds the temperature of the cooling fluid by more than 30° C. anywhere in the reactor.

6. An improved process as set forth in claim 1 wherein the length of said catalyst bed from the gas inlet to the gas exit is at least about 13 feet and the conditions of the process are controlled so that, during a period of at least six months substantially continual operation, the location of the maximum temperature of said gas in said catalyst bed is maintained at not greater than 45% of the length of said bed from the gas inlet of the bed during at least 80% of any reactor operating time in which the gas temperature exceeds the cooling fluid by more than about 30° C. anywhere in the reactor, said length being measured in the direction of gas flow from the bed inlet to the bed exit.

7. An improved process as set forth in claim 1 wherein the process conditions are controlled so that the productivity is at least about 5.0 lbs. maleic anhydride/ft$^3$ catalyst-hour.

8. A process as set forth in claim 1 wherein the conversion is maintained between about 79% and about 90%.

9. A process as set forth in claim 1 wherein the yield of maleic anhydride based on the hydrocarbon feed is at least 49.9%.

10. A process as set forth in claim 1 wherein productivity is at least about 5.5 lbs./hr-ft$^3$ catalyst.

11. A process as set forth in claim 1 wherein the temperature differential between said gas and said cooling fluid does not exceed about 60° C. at any point within the said bed.

12. A process as set forth in claim 1 wherein said region of high activity comprises vanadium/phosphorus oxide catalyst bodies having a surface to volume ratio of at least about 14 cm$^{-1}$.

13. A process for the manufacture of maleic anhydride by passing through a tubular reactor a gas initially containing oxygen, at least about 1.5% by volume of a nonaromatic hydrocarbon having at least four carbon atoms in a straight chain, and a volatile phosphorus compound in a proportion sufficient to provide a phosphorus content of at least about 2×10$^{-5}$% by volume, said tubular reactor containing a fixed bed of a catalyst comprising vanadium, phosphorus and oxygen in which the hydrocarbon and oxygen react to produce maleic anhydride in the vapor phase, said gas and catalyst bed being cooled during the reaction by transfer of heat to a cooling fluid through a wall of said tubular reactor, which comprises:

passing said gas in a single pass through a fixed catalyst bed in which the catalyst activity per unit volume of the bed varies with temperature and hydrocarbon concentration in the direction of flow of gas in such a manner that the reaction rate is promoted by high activity in a region of low temperature and low hydrocarbon concentration within the bed and is restricted by relatively low activity in a critical region within the bed where the combination of temperature and hydrocarbon concentration could otherwise cause the reaction to proceed at an excessive rate or the gas temperature to rise excessively, said critical region comprising a region in which the hydrocarbon concentration exceeds 0.8% by volume and the gas temperature would be more than 30° C. higher than the cooling fluid temperature if the catalyst activity throughout the bed were the same as in said region of high catalyst activity, said activity so varying in the direction of gas flow that the reactor can be operated at initial hydrocarbon concentrations of over 1.5% by volume, an integrated average temperature difference between gas and cooling fluid of at least about 15° C. over that portion of the bed in which the gas temperature exceeds the cooling fluid temperature, a hydrocarbon conversion of a least 79%, and productivity of at least about 5.0 lbs. maleic anhydride per hour-ft$^3$ of catalyst, without said temperature difference between the gas and cooling fluid exceeding 80° C. at any point in the catalyst bed during the course of the reaction; and controlling the rate of introduction of said hydrocarbon into said catalyst bed and the temperature of the reaction so that the conversion of said hydrocarbon is at least about 79% and the temperature differential between said gas and said cooling fluid does not exceed about 80° C. anywhere within said catalyst bed, while the average difference between the temperature of the reacting gas and the temperature of cooling fluid is at least about 15° C. over the portion of the bed in which the gas temperature exceeds the cooling fluid temperature.

14. A process as set forth in claim 13 wherein the catalyst activity in said critical region is lower than in regions, upstream and downstream of said critical region with respect to the flow of said gas, where the concentration of hydrocarbon is less than about 0.5% by volume or where the temperature would be less than 20° C. higher than the temperature of cooling fluid if the catalyst activity throughout the bed were the same as in said region of high catalyst activity.

15. A process as set forth in claim 13 wherein the conditions of the process are controlled so that, when the temperature difference between the gas and the cooling fluid exceeds 30° C. anywhere in the reactor, the maximum temperature of said gas in said catalyst bed occurs at a location that is in said critical region or upstream of said critical region with respect to the direction of gas flow.

16. A process as set forth in claim 13 wherein the catalyst activity per unit of bed volume in said critical region is materially lower than in a downstream region between said critical region and the exit of said bed.

17. A process as set forth in claim 16 in which the gas permeability of said catalyst bed is materially higher in said critical region than it is in said downstream region.

18. A process as set forth in claim 17 wherein the activity of said catalyst in said critical region is at least about 10% lower than the average catalyst activity of the remainder of said bed, and the pressure drop per unit distance in the direction of gas flow in said critical region is at least about 15% lower than the average pressure drop per unit distance in said direction in the remainder of said catalyst bed.

19. A process as set forth in claim 13 wherein said critical region is remote from the gas inlet end of said bed, the average catalyst activity in said critical region is lower than the average catalyst activity in both an upstream region between said inlet and said critical region and a downstream region between said critical region and said exit, and the average gas permeability of the bed is higher in said critical region than in either said upstream region or said downstream region.

20. A process as set forth in claim 13 wherein said hydrocarbon is selected from the group consisting of n-butane, 1-butene, 2-butene, 1,3, -butadiene and mixtures thereof.

21. A process as set forth in claim 13 wherein said critical region comprises a region in which the temperature of said reacting gases would exceed 500° C. if the catalyst activity throughout the bed was the same as in said region of relatively high catalyst activity and the process was operated at a productivity of at least about 5.0 lbs. maleic anhydride/ ft$^3$ catalyst-hour and a hydrocarbon content of at least about 1.5% in said inlet gas.

22. A process as set forth in claim 13 wherein the conditions of the process are controlled so that, during a period of at least six months of substantially continual operation, the location of the maximum temperature of said gas in said catalyst bed is maintained within said critical region or upstream of said critical region with respect to the direction of gas flow for at least 80% of any reactor operating time during which the temperature of the gas exceeds the temperature of the cooling fluid by more than 30° C. anywhere in the reactor.

23. A process as set forth in claim 22 wherein the conditions of the process are controlled so that, during a period of at least one year of substantially continual operation, the location of the maximum temperature of said gas in said catalyst bed is maintained within said critical region or upstream of said critical region with respect to the direction of gas flow for at least 80% of any reactor operating time during which the temperature of the gas exceeds the temperature of the cooling fluid by more than 30° C. anywhere in the reactor.

24. A process as set forth in claim 22 wherein, over at least about 80% of the catalyst life, the maximum temperature of said gas in said catalyst bed is maintained within said critical region or upstream of said critical region for at least 80% of the reactor operating time during which the gas temperature exceeds the cooling fluid temperature by more than about 30° C. anywhere in the reactor.

25. A process as set forth in claim 13 wherein the length of said catalyst bed from the gas inlet to the gas exit is at least about 13 feet and the conditions of the process are controlled so that, during a period of at least six months substantially continual operation, the location of the maximum temperature of said gas in said catalyst bed is maintained at not greater than 45% of the length of said bed from the gas inlet of the bed during at least 80% of any reactor operating time in which the gas temperature exceeds the cooling fluid temperature by more than about 30° C. anywhere in the reactor, said length being measured in the direction of gas flow from the bed inlet to the bed exit.

26. A process as set forth in claim 13 wherein said phosphorus compound comprises an organophosphorus compound.

27. A process as set forth in claim 26 wherein said gas initially contains said phosphorus compound in a proportion sufficient that the phosphorus content of the gas is between about $2 \times 10^{-5}\%$ and about $2 \times 10^{-3}\%$ by volume.

28. A process as set forth in claim 13 wherein gas permeability of the catalyst in the fixed bed varies with temperature and hydrocarbon concentration in the direction of flow of gas, said gas permeability varying in such manner that the pressure drop per unit distance in the direction of gas flow in said critical region is lower than the pressure drop per unit distance in said direction in a downstream region between said critical region and the gas exit of said catalyst bed.

29. A process as set forth in claim 28 further including the steps of
applying a cooling load by flowing a cooling fluid over the outside of said tubular reactor to remove heat generated in the reaction; and
controlling the rate of introduction of said hydrocarbon into said catalyst bed so that the highest temperature of the reacting gases is reached in said critical region;
whereby the reaction is controlled to synthesize maleic anhydride in high productivity and the rate of decay of activity of the catalyst bed is relatively low.

30. A process as set forth in claim 29 wherein the pressure drop per unit distance in said critical region is materially lower than the average pressure drop per unit distance in the remainder of said bed.

31. A process as set forth in claim 30 wherein the pressure drop per unit distance in the direction of gas flow in said critical region is at least 20% lower than the pressure drop per unit distance in the remainder of said bed.

32. A process as set forth in claim 31 wherein the pressure drop per unit distance in the direction of gas flow in said critical region is at least 30% lower than the pressure drop per unit distance in the remainder of said bed.

33. A process as set forth in claim 28 wherein said bed comprises packed discrete catalyst bodies of varying coarseness, the catalyst bodies in said critical region being generally coarser than the catalyst bodies elsewhere in said bed.

34. A process as set forth in claim 33 wherein the catalyst bodies of said bed are of essentially uniform configuration, the catalyst bodies in said critical region having a surface to volume ratio substantially lower than the average surface to volume ration of the catalyst in remainder of said bed.

35. A process as set forth in claim 28 wherein the critical region contains the same active catalyst bodies as a region of higher activity within the bed, but the catalyst bodies in the critical region are diluted with inert bodies which are characterized by a lower friction constant K with respect to the following equation defining pressure drop within packed catalyst beds:

$$Wp = P_{in} - [P_{in}^2 - K_1 T^{1.1} L^{2.76} (SV)^{1.76}]^{0.5}$$

where:
Wp=gas pressure drop through the catalyst bed (or region thereof)
$P_{in}$=reactor inlet pressure (to bed or region), psia
$K_i$=a constant characteristic of the catalyst charge in region i of the bed (friction factor)
T=reactor cooling fluid temperature, °K
L=length of the catalyst bed (or region thereof), ft.
SV=space velocity, $hr^{-1}$.

36. A process as set forth in claim 13 wherein said fixed catalyst bed comprises said critical region which constitutes at least about 10% of the mass of said catalyst bed and is remote from the gas exit end of said bed, and a region downstream of said critical region with respect to the flow of said gas, the catalyst bed in said critical region having a relatively low average surface to volume ratio and relatively low average activity, the catalyst bed in said downstream region having a materially higher average surface to volume ratio and a materially higher average activity than the catalyst in said critical region.

37. A process as set forth in claim 36 wherein said bed is comprised of discrete catalyst bodies, the catalyst bodies in said critical region having a relatively low surface to volume ratio and the catalyst bodies in said downstream region having a relatively high surface to volume ratio.

38. A process as set forth in claim 37 wherein said catalyst bodies are of substantially uniform configuration throughout said bed, whereby the gas permeability of said catalyst bed is greater in said critical region than in said downstream region and the pressure drop per unit distance in the direction of gas flow is lower in said critical region than in said downstream region.

39. A process as set forth in claim 13 wherein the conversion is maintained between about 79% and about 90%.

40. A process as set forth in claim 13 wherein the yield of maleic anhydride based on the hydrocarbon feed is at least 49.9%.

41. A process as set forth in claim 13 wherein productivity is at least about 5.5 lbs./hr-ft³ catalyst.

42. A process as set forth in claim 13 wherein the temperature differential between said gas and said cooling fluid does not exceed about 60° C. at any point within the said bed.

43. A process as set forth in claim 13 wherein said region of high activity comprises vanadium/phosphorus oxide catalyst bodies having a surface to volume ratio of at least about 14 $cm^{-1}$.

44. In a process for the manufacture of maleic anhydride by passing through a tubular reactor a gas initially containing oxygen and a nonaromatic hydrocarbon having a least four carbon atoms in a straight chain, said tubular reactor containing a fixed bed of a catalyst comprising vanadium, phosphorus and oxygen in which the hydrocarbon and oxygen react to produce maleic anhydride in the vapor phase, said gas and catalyst bed being cooled during the reaction by transfer of heat to a cooling fluid through a wall of said tubular reactor, the improvement which comprises:

passing a gas through a fixed catalyst bed, said gas initially containing oxygen, at least about 1.5% by volume of said hydrocarbon and a volatile phosphorus compound in a proportion sufficient to provide a phosphorus content of at least about $2\times10^{-5}$% by volume, the catalyst activity per unit volume of said fixed catalyst bed varying with temperature and hydrocarbon concentration in the direction of flow of gas in such manner that the reaction rate is promoted by high activity in a region of low temperature and low hydrocarbon concentration within the bed and is restricted by relatively low activity in a critical region within the bed where the combination of temperature and hydrocarbon concentration could otherwise cause the reaction to proceed at an excessive rate or the gas temperature to rise excessively, said region of high activity comprising catalyst bodies having a surface to volume ratio of at least about 14 $cm^{-1}$; and controlling the rate of introduction of said hydrocarbon into the catalyst bed and the temperature of the reaction so that the conversion of said hydrocarbon is at least about 79%, the yield of maleic anhydride based on said hydrocarbon is at least about 49.9%, and the temperature differential between said gas and said cooling fluid does not exceed about 60° C. at any point within said bed while the integrated average temperature difference between the reacting gas and the cooling fluid is at least about 15° C. over the portion of the bed in which the gas temperature exceeds the cooling fluid temperature.

* * * * *